United States Patent
Quan

(10) Patent No.: US 11,266,566 B2
(45) Date of Patent: Mar. 8, 2022

(54) DETECTION OF MYOCARDIAL CONTRACTIONS INDICATIVE OF PERFUSION

(71) Applicant: ZOLL MEDICAL CORPORATION, Chelmsford, MA (US)

(72) Inventor: Weilun Quan, Dracut, MA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 482 days.

(21) Appl. No.: 15/580,867

(22) PCT Filed: Jun. 10, 2016

(86) PCT No.: PCT/US2016/037081
§ 371 (c)(1),
(2) Date: Dec. 8, 2017

(87) PCT Pub. No.: WO2016/201367
PCT Pub. Date: Dec. 15, 2016

(65) Prior Publication Data
US 2018/0168923 A1    Jun. 21, 2018

Related U.S. Application Data

(60) Provisional application No. 62/174,480, filed on Jun. 11, 2015.

(51) Int. Cl.
| | |
|---|---|
| *A61H 31/00* | (2006.01) |
| *A61B 5/11* | (2006.01) |
| *A61B 5/00* | (2006.01) |
| *A61N 1/39* | (2006.01) |

(Continued)

(52) U.S. Cl.
CPC .......... *A61H 31/005* (2013.01); *A61B 5/1102* (2013.01); *A61B 5/316* (2021.01);
(Continued)

(58) Field of Classification Search
CPC .................. A61H 31/00; A61H 31/005; A61H 31/004–007; A61B 5/318–33; A61B 5/28; A61B 5/1102; A61B 5/7246
See application file for complete search history.

(56) References Cited

U.S. PATENT DOCUMENTS

| | | | | |
|---|---|---|---|---|
| 3,532,089 A | * | 10/1970 | Arntzenius | ............ A61H 1/003 601/51 |
| 7,488,293 B2 | * | 2/2009 | Marcovecchio | ......... A61N 1/39 600/484 |
| 8,105,249 B2 | * | 1/2012 | Freeman | ........... A61M 16/1075 601/41 |
| 2002/0165471 A1 | * | 11/2002 | Halperin | .............. A61H 31/006 601/41 |

(Continued)

OTHER PUBLICATIONS

Laciar, et al. "Improved Alignment Method for Noisy High-Resolution ECG and Holter Records Using Multiscale Cross-Correlation", Mar. 2003, IEEE Transactions on Biomedical Engineering, vol. 50, No. 3, pp. 344-353 (Year: 2003).*

(Continued)

*Primary Examiner* — Michael J Tsai
(74) *Attorney, Agent, or Firm* — Mintz Levin Cohn Ferris Glovsky and Popeo, P.C.

(57) ABSTRACT

A system for assisting with a cardiopulmonary resuscitation (CPR) treatment being administered to a patient. In one aspect, the system includes electrodes to provide an ECG signal of the patient, one or more sensors configured to measure an intrinsic myocardial wall movement of the patient, and one or more processors. The one or more processors are configured to perform operations including: during the CPR treatment being administered to the patient, receiving an input from the sensor(s), processing the input from the sensor(s) and the ECG signal, determining, based on processing, whether the intrinsic myocardial wall move- (Continued)

ment is indicative of a perfusion movement of the patient's heart, and providing an indication to a user of the system based on the determination.

26 Claims, 12 Drawing Sheets

(51) Int. Cl.
 *A61B 5/316* (2021.01)
 *A61B 5/318* (2021.01)
 *A61N 1/372* (2006.01)
 *A61B 5/026* (2006.01)
 *A61M 16/00* (2006.01)

(52) U.S. Cl.
 CPC ............ *A61B 5/318* (2021.01); *A61B 5/4848* (2013.01); *A61B 5/7246* (2013.01); *A61H 31/006* (2013.01); *A61H 31/007* (2013.01); *A61N 1/39044* (2017.08); *A61N 1/3993* (2013.01); *A61B 5/0006* (2013.01); *A61B 5/026* (2013.01); *A61B 2505/01* (2013.01); *A61H 2031/001* (2013.01); *A61H 2031/003* (2013.01); *A61H 2201/0184* (2013.01); *A61H 2201/107* (2013.01); *A61H 2201/1253* (2013.01); *A61H 2201/5007* (2013.01); *A61H 2201/5043* (2013.01); *A61H 2201/5058* (2013.01); *A61H 2201/5079* (2013.01); *A61H 2201/5084* (2013.01); *A61H 2201/5097* (2013.01); *A61H 2230/04* (2013.01); *A61H 2230/30* (2013.01); *A61M 16/0078* (2013.01); *A61N 1/37282* (2013.01)

(56) References Cited

U.S. PATENT DOCUMENTS

| 2004/0039419 A1* | 2/2004 | Stickney .............. A61B 5/1102 607/5 |
| 2004/0039420 A1* | 2/2004 | Jayne .................... A61B 5/1107 607/5 |
| 2006/0009809 A1* | 1/2006 | Marcovecchio ....... A61H 31/00 607/5 |
| 2008/0208273 A1* | 8/2008 | Owen ................ A61B 5/02416 607/6 |
| 2008/0281214 A1 | 11/2008 | Elle et al. |
| 2012/0016179 A1* | 1/2012 | Paradis ................. A61H 31/005 600/17 |
| 2013/0085404 A1* | 4/2013 | de Melis ............. A61B 5/0245 600/513 |
| 2014/0276131 A1* | 9/2014 | Geheb ...................... A61B 5/11 600/484 |
| 2015/0133806 A1* | 5/2015 | Airaksinen .......... A61B 5/1102 600/513 |
| 2016/0206504 A1* | 7/2016 | Giarracco ............ A61B 5/0261 |

OTHER PUBLICATIONS

Milesi, Ilaria, et al. "Measurement of Local Chest Wall Displacement by a Custom Self-Mixing Laser Interferometer", Aug. 2011, IEEE Transactions on Instrumentation and Measurement, vol. 60, No. 8, pp. 2894-2901 (Year: 2011).*

International Search Report and Written Opinion dated Aug. 29, 2016 in International Application No. PCT/US2016/037081, 14 pgs.

* cited by examiner

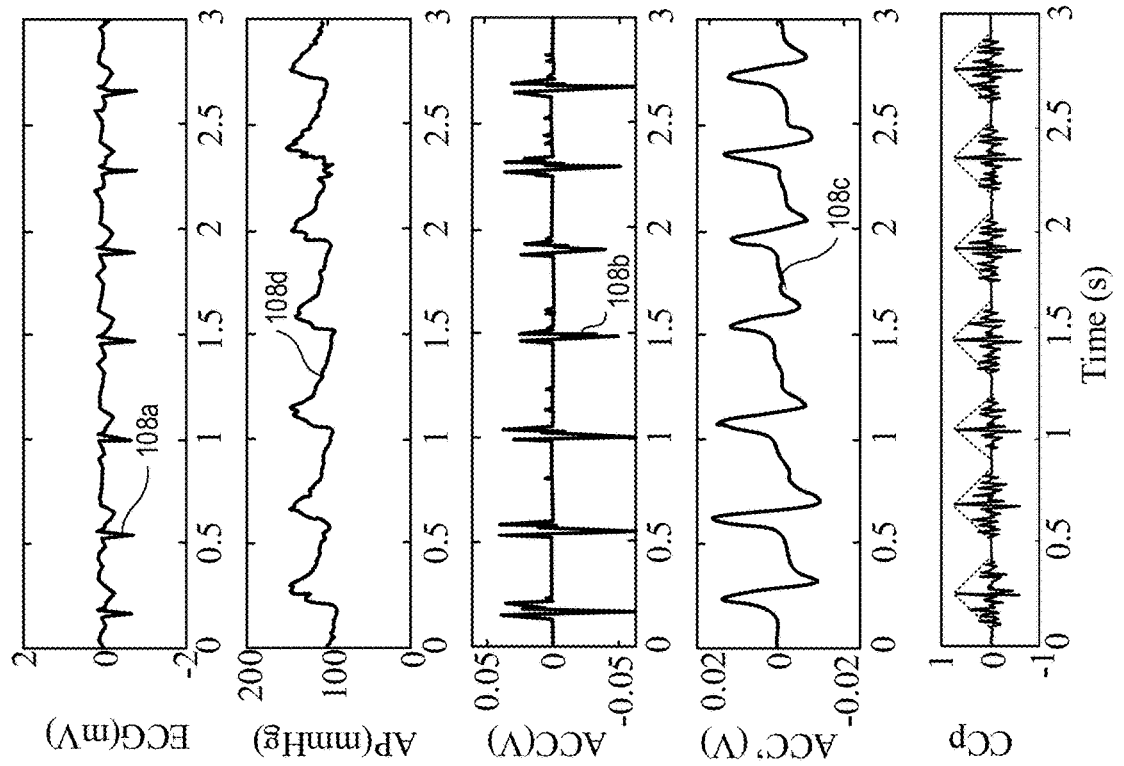
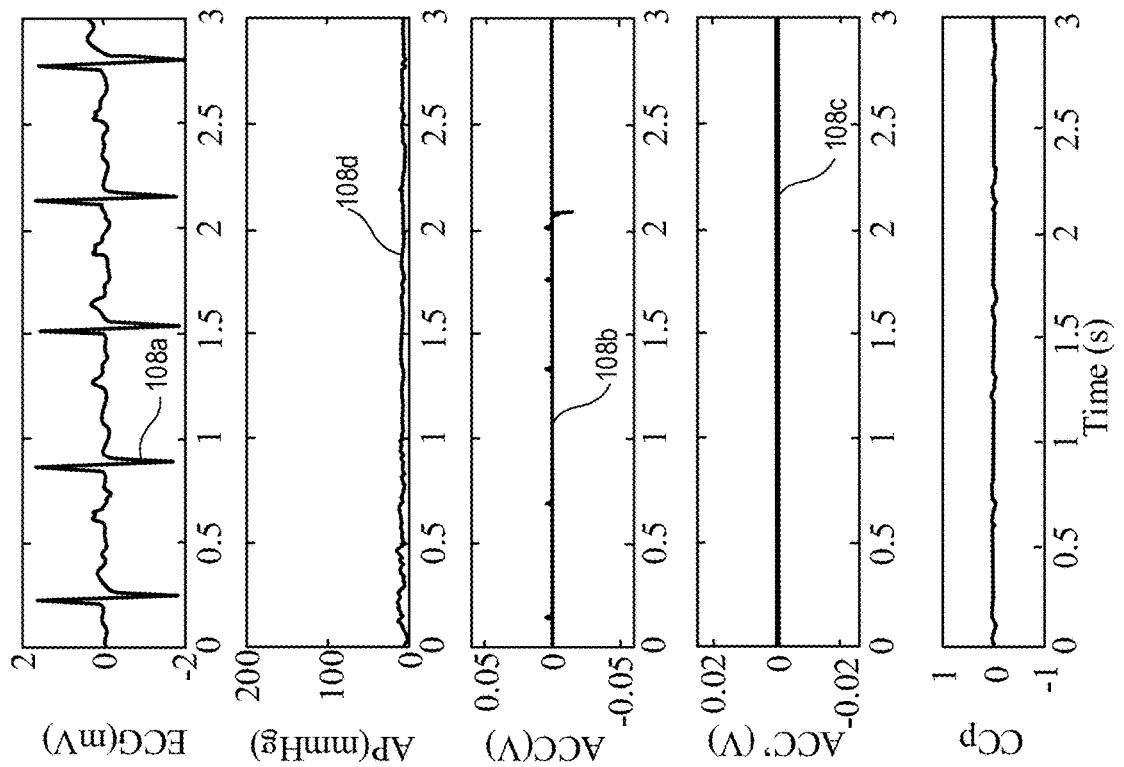
FIG. 1E
FIG. 1F

DETECTION OF MYOCARDIAL CONTRACTIONS INDICATIVE OF PERFUSION

CROSS-REFERENCE TO RELATED APPLICATION

This application is a U.S. National Phase Application under 35 U.S.C. § 371 of International Patent Application No. PCT/US2016/037081, filed on Jun. 10, 2016, which claims benefit of priority to U.S. Provisional Application Ser. No. 62/174,480, filed on Jun. 11, 2015, the entire contents of both are hereby incorporated by reference.

TECHNICAL FIELD

This document relates to identification and management of cardio-pulmonary resuscitation (CPR), and in particular to systems and techniques for detecting myocardial contractions indicative of cardiac movement capable of perfusion.

BACKGROUND

Pulseless electrical activity (PEA) is a clinical condition characterized by lack of palpable pulse in the presence of organized cardiac electrical activity. PEA sometimes occurs in out-of-hospital cardiac arrest. PEA could also occur after electrical defibrillation is delivered. Some therapies for PEA include chest compression to move the blood, ventilation to correct hypoxia and administration of epinephrine after the reversible causes of the PEA have been identified and corrected.

SUMMARY

In a general aspect, a system includes a sensor attached to a patient and a first computing device including a processor coupled to a memory. The system configured to assist with CPR treatment includes: electrodes to provide an ECG signal of the patient, a sensor configured to measure an intrinsic myocardial wall movement of the patient, and one or more processors. The one or more processors are configured to perform operations including: during the CPR treatment being administered to the patient, receiving an input from the sensor, processing the input from the sensor and the ECG signal, determining, based on processing, whether the intrinsic myocardial wall movement is indicative of a perfusion movement of the patient's heart, and providing an indication to a user of the system based on the determination.

Implementations can include one or more of the following features. The sensor can include a motion sensor. The motion sensor can include an accelerometer, or other sensor capable of measuring movement of a myocardial wall.

In some implementations, processing can include performing a correlation between the ECG signal and the intrinsic myocardial wall movement. Performing the correlation can include determining a peak correlation coefficient between the ECG signal and the intrinsic myocardial wall movement. Processing can include comparing the peak correlation coefficient to a threshold that is between approximately 0.1 and 0.5. Determining whether the intrinsic myocardial wall movement is indicative of a perfusion movement can correspond to the peak correlation coefficient exceeding the threshold. Performing the correlation can include determining a shape of a correlation function between the ECG signal and the intrinsic myocardial wall movement. Determining whether the intrinsic myocardial wall movement is indicative of a perfusion movement is indicated by the shape being triangular. Providing feedback can include an indication to stop chest compressions. Providing feedback can include indicating the presence of a perfusion movement. The perfusion movement can include one or both of a residual left heart movement or residual right heart movement.

In some implementations, the system can also include at least one of a mechanical compression device, an inflatable vest, a nerve stimulator, and a suction based compression-decompression device to administer the CPR treatment. The system can also include a defibrillator configured to provide electrotherapy. Determining, based on processing, further can include determining a degree of electromechanical dissociation between the input from the sensor and the ECG signal. The degree of electromechanical dissociation is determined based on the magnitude of the intrinsic myocardial wall movement. The degree of electromechanical dissociation is determined based on the time delay between the ECG signal and the intrinsic myocardial wall movement. The degree of electromechanical dissociation is determined based on the magnitude of the intrinsic myocardial wall movement and the time delay between the ECG signal and the intrinsic myocardial wall movement. Providing feedback can include at least one of an indication to synchronize chest compression to cardiac systole or an indication to continue chest compressions.

In a general aspect, a method for assisting with a cardio-pulmonary resuscitation (CPR) treatment administered to a patient can include: receiving, by one or more processors, an ECG signal associated with the patient, receiving, by one or more processors, an input from a sensor configured to detect an intrinsic myocardial wall movement of the patient, processing, by one or more processors, the input from the sensor and the ECG signal, determining, by one or more processors and based on processing, whether the intrinsic myocardial wall movement is indicative of a perfusion movement of the patient's heart, and providing, by one or more processors, a feedback including an indication to terminate the CPR treatment.

In a general aspect, a system for assisting with a cardio-pulmonary resuscitation (CPR) treatment to be administered to a patient can include: electrodes to provide an ECG signal of the patient, a motion sensor configured to detect an intrinsic myocardial wall movement of the patient, and one or more processors configured for during the CPR treatment being administered to the patient, receiving an input from the motion sensor, processing the input from the motion sensor and the ECG signal, determining, based on processing, whether the intrinsic myocardial wall movement is indicative of a perfusion movement of the patient's heart, and determining CPR treatment based on the determination.

In some implementations, the motion sensor is an accelerometer. The intrinsic myocardial wall movement of the patient is detected during a period when CPR chest compressions are not being delivered. The determination can include at least one of stopping chest compressions, synchronizing chest compression to cardiac systole or an indication to continue chest compressions. The determination can further include synchronizing ventilation with the cardiac cycle. The chest compressions are delivered by a rescuer and the determination of CPR treatment is indicated to the rescuer by a prompt. The chest compressions are delivered by a mechanical chest compression device and wherein the controller of the mechanical chest compression device is configured to stop chest compressions, synchronize chest compression to cardiac systole or continue chest compressions upon receiving a determination of the CPR treatment. The system can further include an intrathoracic pressure regulation device configured to enhance negative intrathoracic pressure to promote blood flow into the heart.

The details of one or more implementations are set forth in the accompanying drawings and the description below. Other features and advantages will be apparent from the description, drawings, and claims.

DESCRIPTION OF DRAWINGS

FIG. 1E is a graph that represents signals acquired from a CPR feedback sensor in a porcine model presenting non-perfusion.

FIG. 1F is a graph that represents signals acquired from a CPR feedback sensor in a porcine model presenting perfusing rhythm.

DETAILED DESCRIPTION

CPR, in which a rescuer administers chest compressions to a patient, is a typical first treatment for PEA. For example, CPR can be administered while potential underlying causes of PEA are identified and treated. CPR treatment and/or other treatments (e.g., administration of epinephrine and vasopressin) that are simultaneously applied with CPR can restore cardiac perfusion (e.g., return of spontaneous circulation), which can be identified by monitoring cardiac mechanics. However, maintaining CPR after the restoration of cardiac mechanics can be detrimental to the patient. A device can be used to assist with CPR treatment, e.g., by identifying when PEA is and is not occurring, and providing feedback to a rescuer about when to administer and when not to administer CPR. Determination and classification of PEA can be based on information associated with synchronized cardiac electromechanics, including intrinsic myocardial wall movement (e.g., myocardial contractility generated by ionic flow throughout the myocardium without an identifiable external cause) coordinated with myocardial electricity. For example, PEA can be detected by analyzing ECG signals in association with intrinsic cardiac mechanical movements that are indicative of a perfusion movement of the patient's heart. One or more sensors such as a motion sensor (e.g., accelerometer) may be used to detect movement of the chest wall or other surface of the patient that moves due to internal blood flow. Such motion information may be used to classify the type of rhythm the patient is experiencing, e.g., PEA, perfusion or other rhythm.

Figure 1A:
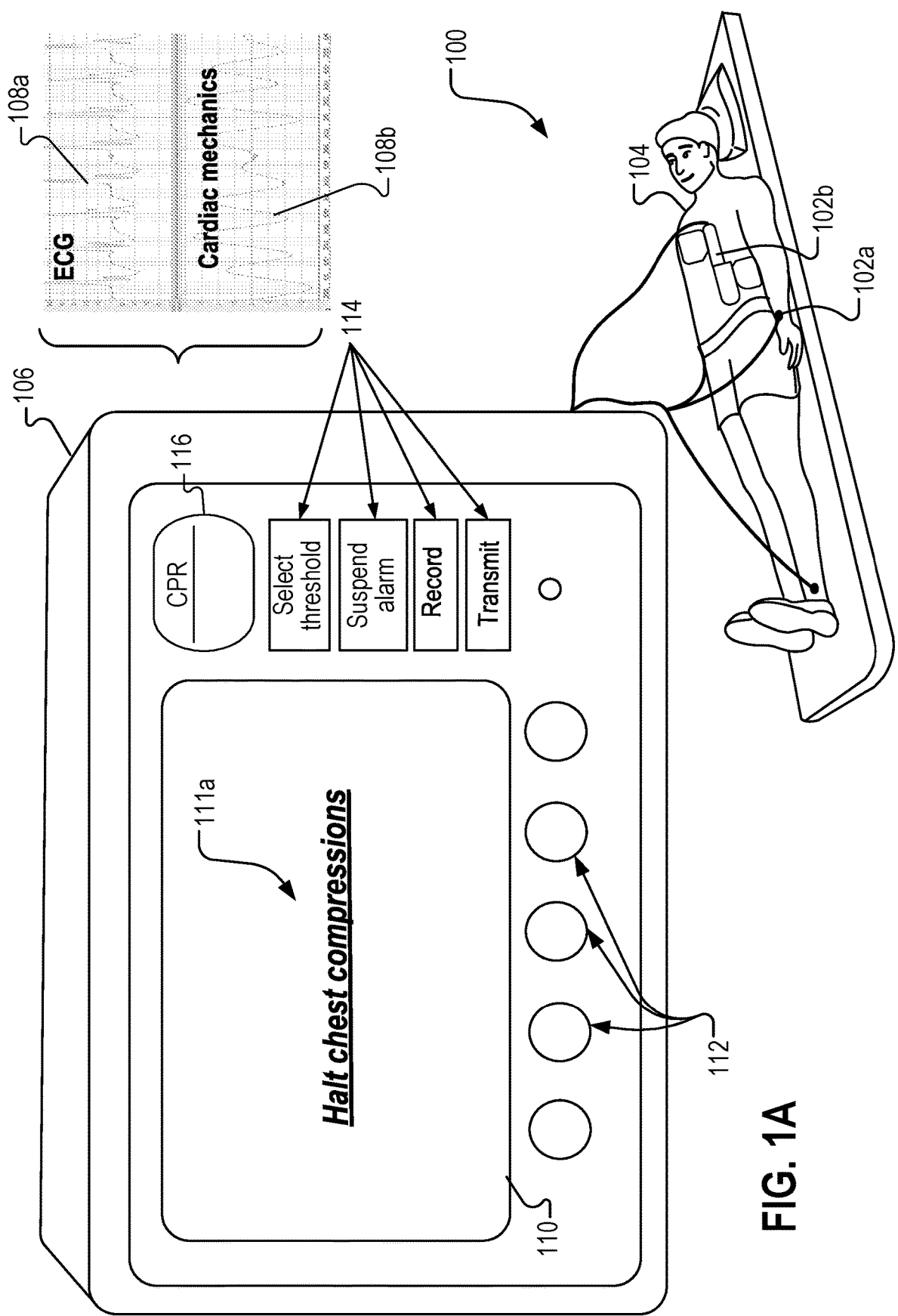
FIGS. 1A and 1B are schematic illustrations of an example system for assisting with CPR treatment.
Figure 1B:
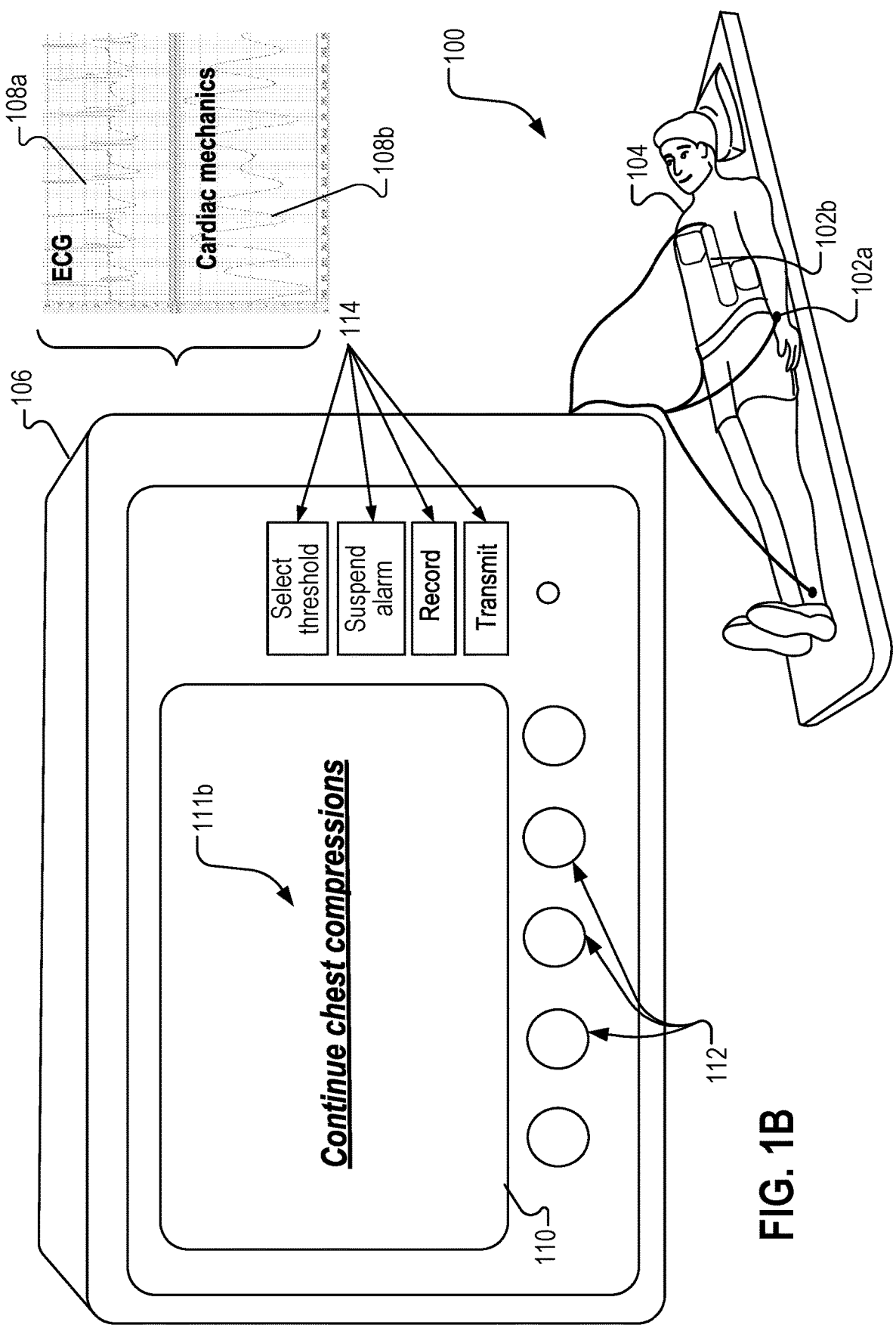

FIGS. 1A and 1B illustrate an example patient monitoring configuration 100. The example, patient monitoring configuration 100 includes multiple sets of sensors 102a and 102b that can be attached to various locations on the body surface of the patient 104. The sensors 102a and 102b are electrically coupled to a patient monitoring device 106 which provides output 111a and 111b on a user interface 110 based on input received from the sensors 102. The output can include directions to a user of the monitoring device 106, e.g., directions specifying whether or not to continue administering CPR to the patient 104. Depending on the input, the output 111a (FIG. 1A) can specify to halt chest compressions, or, alternatively output 111b (FIG. 1B) can specify to continue chest compressions at a predetermined rate or at a rate and duration synchronized to a detected cardiac mechanical signal (e.g., intrinsic movement of myocardium).

Sensors 102a can be configured to detect an ECG signal. In some examples, sensors 102a can include a plurality (e.g., two or more) of ECG electrodes. Sensors 102b can be configured to measure a cardiac mechanical signal. In some examples, the sensors 102b can include CPR sensors configured to measure depth and rate of compressions exerted by the user of the system 100 that can be used to optimize the synchronization of CPR with cardiac mechanics. In some examples, the sensors 102b can be attached to defibrillation electrodes (e.g., CPR-D-padz, CPR Electrodes manufactured by ZOLL Medical®, Chelmsford Mass.) configured to deliver a defibrillation signal. In some examples, the sensors can include a motion sensor. Where the sensor 102b is a motion sensor, it may be placed on the chest of the patient, for example above the sternum. The motion sensor can be an accelerometer (configured to detect chest movements of the patient during a series of individual chest compressions and provide as output an accelerometer signal), a velocity sensor, or any other appropriate motion sensor for recording a displacement of the patient's chest. Other kinds of sensors 102b can be used, for example, sensors 102b can include a laser interferometer, elastic band, or other sensor for measuring chest wall motion characteristic of an intrinsic myocardial wall movement of the patient.

In some examples, the monitoring device 106 is part of a system including a manual chest compression monitor or mechanical chest compression device. The system 100 may include a respiratory device configured to provide automatic or assisted ventilation. For example, the respiratory device can include a facial mask and a housing that is operably attached to the mask. The housing can include a mouth piece and at least one inflow valve which prevents respiratory gases from entering the lungs until a threshold negative intrathoracic pressure level is exceeded at which time the inflow valve opens. The housing can further include an air chamber or a ventilation bag in communication with the mouth piece, and a valve member to force air from the air chamber into the facial mask when air is supplied through the mouth piece. Using the respiratory device (which may comprise a respiratory sensor), a rescuer can periodically ventilate the patient with air stored in the chamber, in a controlled fashion.

The portion of the body surface of the patient 104 selected for attaching the sensors 102a and 102b can depend on the type of the selected sensor. Example portions of the body surface of the patient 104 that can be selected for attaching the sensors 102a and 102b include the chest, the neck, the abdomen and the limb of the patient 104.

The sensors 102a and 102b can be electrically coupled to a patient monitoring device 106. An example of a patient monitoring device 106 can be a standard ECG monitoring device, a portable ECG monitoring device, a defibrillator, a smartphone, a personal digital assistant (PDA), a laptop, a tablet personal computer (PC), a desktop PC, a set-top box, an interactive television and/or combinations thereof or any other type of medical device capable to record and process ECG signals and cardiac mechanical signals. For example, the sensors 102a and 102b can be implemented in or coupled to standard medical devices, such as X-Series monitors and defibrillators produced by ZOLL Medical®, Chelmsford Mass.

The patient monitoring device 106 can be configured to provide feedback to a user of the monitoring device 106. The feedback can include a CPR treatment recommendation, for example whether to provide chest compressions (e.g., "halt chest compressions" as illustrated in FIG. 1A or "continue chest compressions" as illustrated in FIG. 1B) to modify chest compressions, whether to provide or modify ventilation, etc. The feedback can be based on a result of background processing of an ECG signal 108a and a cardiac mechanical signal 108b. The cardiac mechanical signal 108b can depict intrinsic myocardial wall movement of the patient undergoing CPR treatment indicative of a perfusion movement, such as one or both of a residual left heart movement or residual right heart movement.

The monitoring device 106 enables user input via the user interface 110 and additional control buttons 112 and 114. In some implementations, the control buttons 114 can enable a user to initiate, stop or modify particular actions that can be performed by the patient monitoring device 106. Actions that can be initiated, stopped or modified by using the buttons 114 can include the selection of processing method, selection of an alarm threshold, suspension of alarm, recording of data and transmitting data over the network to a remote device.

The monitoring device 106 can also include a metronome (e.g., a rate indicating prompt) and audible instructional prompts to perform CPR at a given compression rate. For example, the user can be initially prompted with the use of a metronome (e.g., a rate indicating prompt) and audible instructional prompts to perform chest compressions according to AHA guidelines (100 cpm, 4-5 cm compression). The metronome can also be used to prompt the delivery of ventilation.

Based on processing the ECG signal 108a and the derived intrinsic myocardial wall movement 108b, the compression rate and compression depth can be altered from the recommended guideline via the user interface 110, the metronome and voice prompts to improve circulation. For example, the feedback control system via the metronome and audible prompts can assist the user in maintaining or stopping chest compression or authorizing a mechanical CPR device to terminate chest compression, as described with reference to FIGS. 3 and 4. Examples of mechanical CPR devices include an inflatable vest, a nerve stimulator, or a suction based compression-decompression device. Also, the feedback control system may control a ventilator or provide instructions to a user to provide ventilation. For example, the controller may control the ventilation rate and/or volume, or provide prompts to a user regarding ventilation rate and/or volume. In addition, the CPR devices may include intrathoracic pressure regulators, for example, devices to enhance the extent and duration of negative intrathoracic pressure to promote blood flow into the heart and lungs.

Figure 1C:
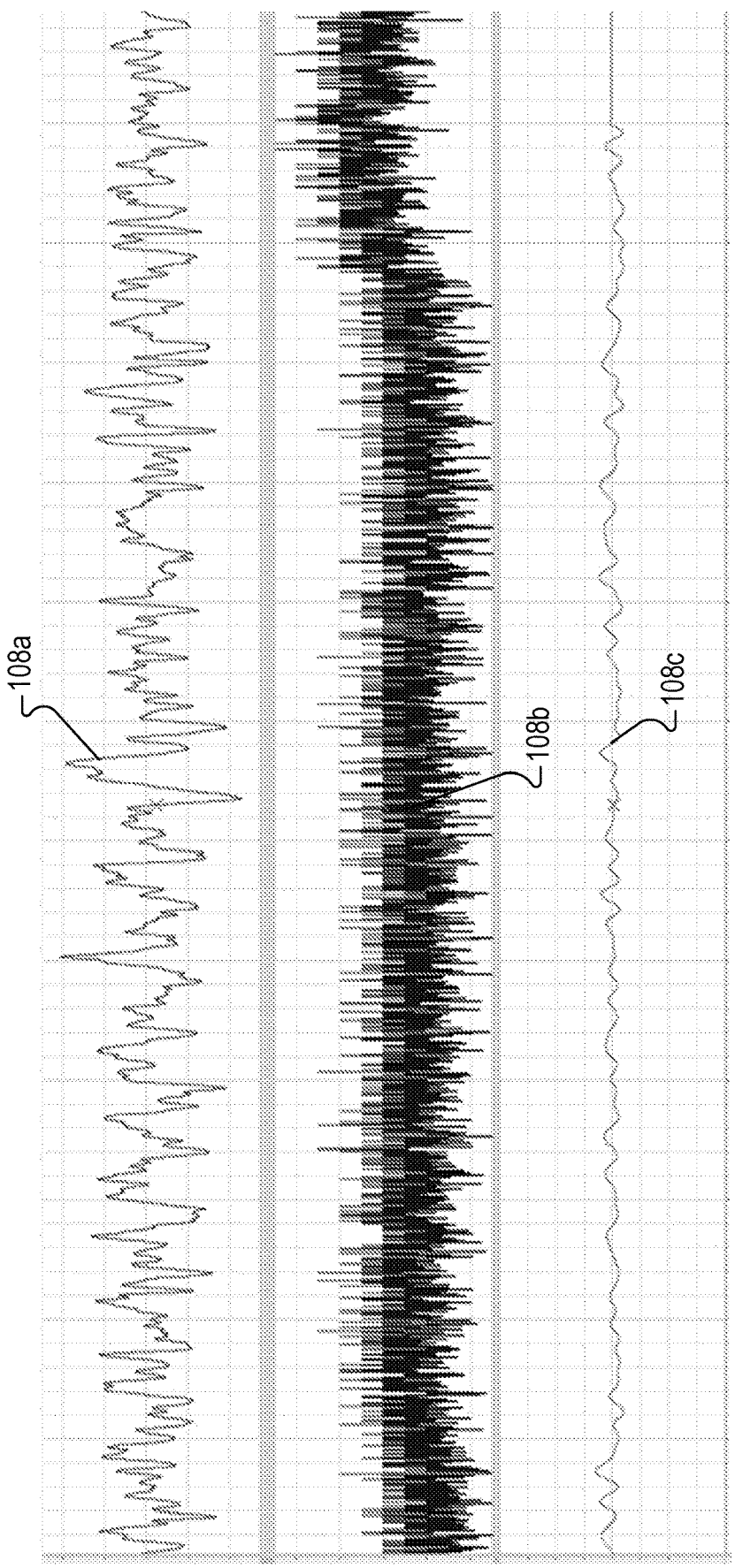
FIG. 1C is a graph that represents signals acquired from a CPR feedback sensor in a human presenting non-perfusion.
Figure 1D:
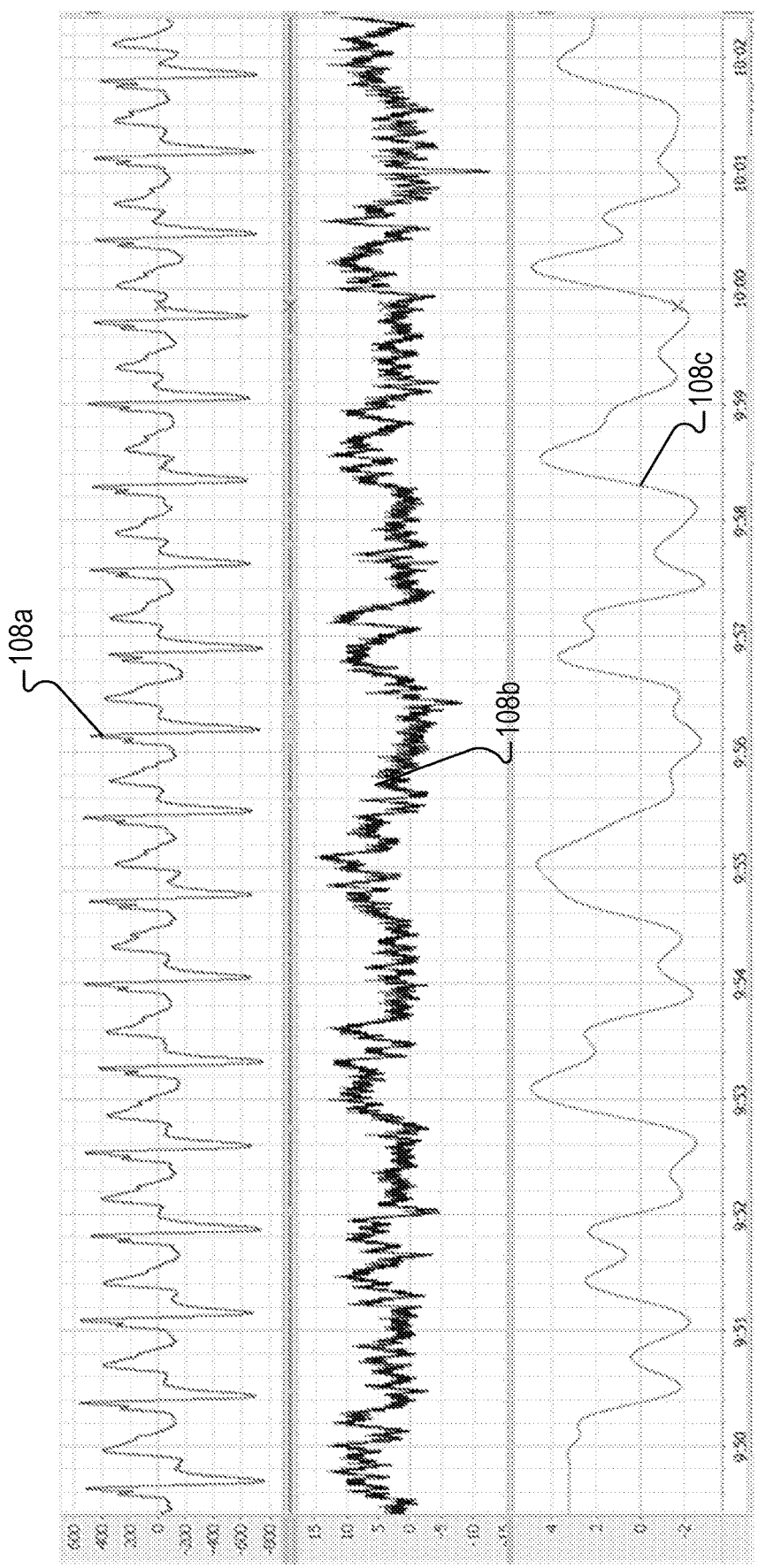
FIG. 1D is a graph that represents signals acquired from a CPR feedback sensor in a human presenting perfusing rhythm.

FIGS. 1C and 1D show example graphs that represent signals 108a, 108b, and 108c associated to a non-perfusing and a perfusing human rhythm, respectively. The experimental data was acquired and analyzed to determine the correlation between the ECG signal 108a and the intrinsic myocardial wall movement 108c derived from a raw accelerometer signal 108b. Digitized ECG recording 108a and the accelerometer signal 108b were downloaded from an AED used for an emergency medical service (EMS). Accelerometer signals were arbitrarily selected from pre-shock pauses where ventricular fibrillation (VF) was the underlying rhythm. A narrow band-pass filter with a center frequency between 0.5 to 5 Hz was applied to the accelerometer signal 108b to eliminate high-frequency noise and generate the intrinsic myocardial wall movement 108c. Cross-correlation function was then calculated between the ECG signal 108a and the intrinsic myocardial wall movement 108c to obtain the peak correlation coefficient (CCp).

The set of data illustrated in FIG. 1C representing non-perfusing rhythms can be compared to the arbitrarily selected sample from organized rhythms identified in post-shock pauses during rhythm check, as illustrated in FIG. 1D. The organized rhythm illustrated in FIG. 1D was confirmed to be a perfusing rhythm by the presence of systolic blood pressure measurements (>100 mmHg). The intrinsic myocardial wall movement 108c can depict cardiac mechanics of the patient undergoing CPR treatment indicative of a perfusion movement, such as one or both of a residual left heart movement or residual right heart movement with respect to success of subsequent defibrillation attempts.

A study including 20 perfusing rhythm epochs and 20 non-perfusing rhythm epochs from a total of 40 patients was performed. The intrinsic myocardial wall movements 108c in perfusing rhythms (as illustrated in FIG. 1D) showed periodic oscillations synchronized with R waves in the ECG signal 108a. In the non-perfusing rhythm group, intrinsic myocardial wall movements 108c (as illustrated in FIG. 1C) did not show periodic oscillations. The peak amplitude of accelerometer tracings was 0.021+0.008 (G) in perfusing rhythms, and 0.019+0.014 (G) in non-perfusing rhythms. With CCp as the classification variable to predict perfusing rhythm, the area under the ROC curve was 0.87. Using a CCp of 0.128 as cut-off resulted in a value of 0.7 for sensitivity, specificity and positive predictive value for perfusing rhythm.

FIGS. 1E and 1F show example graphs that represent signals 108a, 108b, 108c, and 108d associated to a non-perfusing and a perfusing rhythm in a porcine model, respectively. The signals 108a, 108b and 108d were extracted from a set of signals collected from 50 male adult pigs weighing 35-42 kg, with prolonged cardiac arrest (45 ventricular fibrillation and 5 asphyxia) and CPR. The porcine models were anesthetized, endotracheally intubated and mechanically ventilated. The ECG signal 108a, the raw accelerometer signal 108b and the arterial blood pressure signal 108d were synchronously recorded at a sample rate of 300 Hz. The accelerometer signal 108b was acquired from an accelerometer-based CPR sensor that was placed on the surface of the porcine model's chest over the heart. Aortic and right atrial pressures (signal 108d) were invasively monitored and coronary perfusion pressure (CPP) calculated. Carotid blood flow (CBF) was continuously monitored by a transonic flow probe. VF was electrically induced and left untreated for 3 minutes before delivering the first shock. If the post countershock rhythm remained in VF a second shock was delivered after an additional period of VF from 1 to 2 minutes. Counter shocks were continued until PEA was obtained. If shock resulted in a perfusing rhythm, VF was re-induced. After PEA was induced, 15 seconds of chest compression or medium energy pacing were delivered to the porcine model per another concurrent protocol. The rate of standard chest compressions was 100 per minute. The porcine models were randomized to receive synchronized or standard chest compressions for 15 seconds, with continuous alternation of therapy for the maximum 120 seconds before the first administration of epinephrine. A standard CPR rescue protocol continued for maximum 20 minutes. If a perfusing rhythm was achieved, the porcine model received at least 4 minutes for recovery before the study sequence was repeated.

The signals 108a, 108b, 108c, and 108d correspond to a time interval of 3 seconds, extracted from chest compression pauses. Perfusing rhythm was defined as systolic arterial pressure larger than 60 mmHg and pulse pressure larger than 10 mmHg in the presence of an organized rhythm. The accelerometer signal 108b was pre-processed using a narrow band-pass filter with the center frequency from 0.5 to 7.5 Hz. Cross-correlation function was calculated between ECG signal 108a and intrinsic myocardial wall movement 108c to obtain the peak CCp. Area under the receiver operating characteristic curve was used to evaluate the ability of CCp to detect a perfusing rhythm.

A total of 216 segments were obtained with 63 cases of perfusing rhythm and 153 cases of PEA. FIGS. 1E and 1F show examples of PEA and perfusing rhythm, respectively. The intrinsic myocardial wall movement 108c in perfusing rhythm shows periodic oscillations synchronized with R waves of the ECG signal 108a (FIG. 1F). The intrinsic myocardial wall movement 108c shows no periodic oscillations for PEA (FIG. 1E). Compared with PEA, heart rate (159.0±50.7 vs. 86.0±44.9 bpm, p<0.01), systolic arterial pressure (143.3±38.3 vs. 18.9±13.3 mmHg, p<0.01), pulse pressure (42.3±14.5 vs. 5.6±8.3 mmHg, p<0.01), and CCp (0.443±0.171 vs. 0.096±0.085, p<0.01) were significantly higher for perfusing rhythm. The area under the receiver operating characteristic curve was 0.95 when CCp was used to differentiate perfusing rhythm from PEA. Using a CCp cut-off threshold of 0.244, the sensitivity and specificity were 90.5%, respectively.

Figure 2:
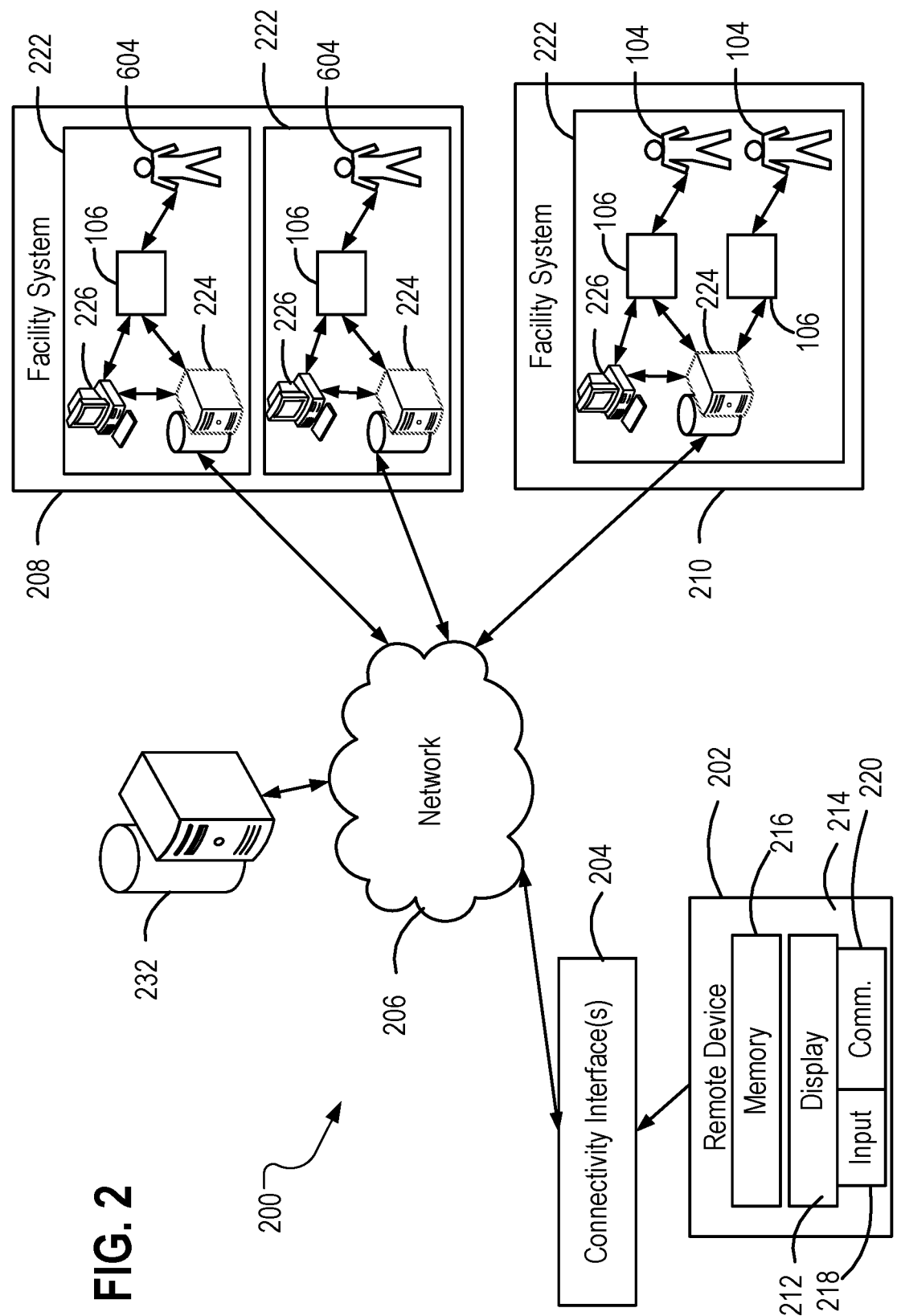
FIG. 2 is a schematic illustration of another example system for assisting with CPR treatment.

FIG. 2 shows an example system 200 that includes monitoring of PEA and in particular identification of a perfusion movement to determine whether to provide feedback to a rescuer to terminate chest compressions. The cardiac electromechanical activity of a patient can be continuously monitored by the patient monitoring device 106, which includes monitoring of ECG signals and intrinsic myocardial wall movements. The patient monitoring device 106 can include the patient information system 224 and the computer interface 120, forming a part of or a complete system for indicating the termination or the adjustment of chest compressions.

The system 200 for indicating that chest compressions should be suspended or modified based on the identification of an event (e.g., identification of cardiac perfusion or degree of electromechanical dissociation). Different facility systems 208 and 210 can process input data according to different rules. For example, in some cases, patient data is transferred to a remote device 202 at the identification of an event (e.g., occurrence of synchronized cardiac electromechanics including intrinsic cardiac mechanics). In other cases, data can be transferred upon a request of a user of the remote device 202.

The remote device 202 can include any number of devices. Such devices include, but are not limited to, a mobile phone, a smartphone, a personal digital assistant (PDA), a laptop, a tablet personal computer (PC), a desktop PC, a set-top box, an interactive television and/or combinations thereof. The remote device 202 includes a display 212, a processor 214, memory 216, an input interface 218, and a communication interface 220.

The remote device 202 can communicate wirelessly through the communication interface(s) 204, which can include digital signal processing circuitry. The communication interface(s) 204 can provide communications under various modes or protocols including, but not limited to, GSM voice calls, SMS, EMS or MMS messaging, CDMA, TDMA, PDC, WCDMA, CDMA2000, and/or GPRS. Such communication can occur, for example, through a radio-frequency transceiver (not shown). Further, the remote device can be capable of short-range communication using features including, but not limited to, Bluetooth and/or WiFi transceivers (not shown).

The remote device 202 communicates with the network 206 through the connectivity interface(s) 204. The connectivity interface(s) 204 can include, but is not limited to, a satellite receiver, cellular network, a Bluetooth system, a Wi-Fi system (e.g., 202.x), a cable modem, a DSL/dial-up interface, and/or a private branch exchange (PBX) system. Each of these connectivity interfaces 204 enables data to be transmitted to/from the network 206. The network 206 can be provided as a local area network (LAN), a wide area network (WAN), a wireless LAN (WLAN), a metropolitan area network (MAN), a personal area network (PAN), the Internet, and/or combinations thereof.

In the systems of FIG. 2, the first facility system 208 includes a plurality of facilities 222, and the second facility system 210 includes a single facility 222. Each facility 208, 210 or 222 includes an associated patient information system 224, computer system 226, and patient monitoring device(s) 208. In some implementations, the patient information system 224 can include a cardiology information system. Although the system architecture 200 includes a patient information system 224 located at each facility 222, it is contemplated that the facilities 222 can communicate with a common patient information system 224 that is remotely located from either facility 222, or that is located at one of the facilities 222 within the facility system 208, 210.

Each patient monitoring device 106 is configured to monitor physiological characteristics of a particular patient 209, to generate data signals based thereon. In the example context of the present disclosure, the patient monitoring devices 208 include ECG monitoring devices, cardiac mechanical signal monitoring devices and one or more processors. The data signals are communicated to the patient information system 224 which can collect patient data based thereon, and store the data to a patient profile that is associated with the particular patient. The patient monitoring device 106 can communicate with the patient information system 224 and/or the computer interface 120 via a direct connection, or remotely through a network (not shown) that can include, but is not limited to, a LAN, a WAN, a WLAN, and/or the Internet.

In some cases, the patient data can include ECG signals, cardiac mechanical signals, results of data processing and, optionally, additional coregistered physiological data. The patient data can be made available for display on remote device 202 and/or directly at the patient monitoring device 208. A healthcare provider (e.g., a technician, a nurse and/or physician) can augment the patient data by inputting patient information that can be stored by a patient information system 224. A healthcare provider can provide instructions to a remote rescuer, based on the data, regarding the CPR treatment (for example, whether to stop, continue or modify CPR). More specifically, the healthcare provider can input patient information corresponding to a particular patient 209, which patient information can be stored to the patient profile.

As discussed above, each patient information system 224 stores patient data that can be collected from the patient monitoring devices 208, as well as additional patient information, that can include information that is input by a healthcare provider. The patient information system 224 communicates the patient data and/or the additional patient data to a server 232, or a virtual server that runs server software components, and can include data storage including, but not limited to, a database and/or flat files. Each patient information system 224 communicates with the server 232 via a direct connection, or remotely through a network (not shown) that can include, but is not limited to, a LAN, a WAN, a WLAN, and/or the Internet.

The server 232 can communicate ancillary information (e.g., treatment plan) to the patient information system 224. In some implementations, each facility system 208, 210 can include a corresponding server 232. In such an arrangement, each patient information system 224 communicates patient data, and/or additional patient data to the server 232. The example system architecture of FIG. 2, provides for the remote location of data collection at the server 232. In such implementations, the server 232 can be provided at a third-party site, remote from any of the facilities 222, or facility systems 208, 210.

Figure 3:
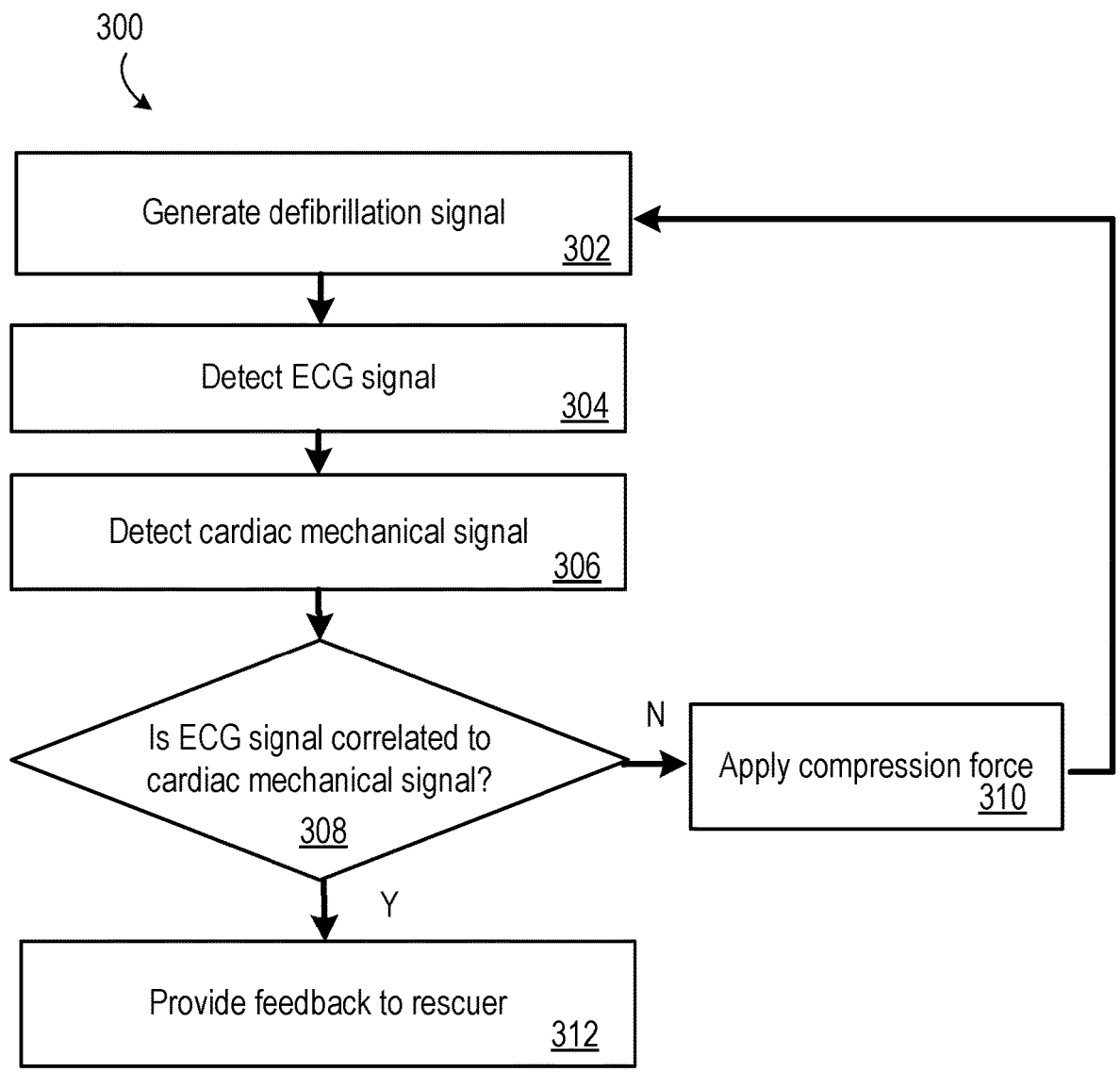
FIG. 3 is a flow chart of an example process for assisting with CPR treatment.

FIG. 3 shows an example process 300 for assisting with CPR treatment based on identification of cardiac perfusion. In some implementations, the method 300 is implemented by the example patient monitoring device described herein with reference to FIGS. 1, 2 and 5. However, other implementations are possible.

At step 302, a defibrillation signal is generated to treat cardiac arrest in a patient. For example, defibrillation pads are attached to the patient to provide electrotherapy during the CPR treatment. Electrotherapy can include delivery of a therapeutic defibrillation current of standard or particularly selected duration, frequency and voltage.

At step 304, an ECG signal is detected. The ECG signal can be received from any appropriate source of patient ECG data. For example, ECG data can be received in real-time from two or more ECG electrodes attached to a patient or previously recorded data can be received from a storage device. ECG data can be of any appropriate type. ECG data can be recorded from a plurality of lead sites on the surface of the patient's body. In some implementations, standard 12-lead ECG recordings (e.g., leads I, II, III, aVR, aVF, aVL, V1, V2, V3, V4, V5 and V6) can be derived based on signals retrieved with 10 ECG electrodes. Any appropriate number of ECG electrodes, attached to appropriate body sites, can be used. Examples of other ECG lead systems include the "Frank" electrode lead system (e.g., 6 electrodes), the McFee-Parungao Lead System, the SVEC III Lead System, Fischmann Barber-Weiss Lead System, and the Nelson Lead System. Other examples include addition of right-sided precordial leads, posterior leads, leads placed in higher or lower intercostal spaces, and the like.

In some implementations, ECG detection includes ECG signal pre-processing. For example, the patient monitoring device can perform real time ECG signal pre-processing. Real time ECG signal pre-processing can include removing the DC component with a high-pass filter, amplifying the ECG signal, limiting the signal bandwidth with a low-pass filter and digitally sampling the ECG signal. Real time ECG signal pre-processing can also include a beat detection algorithm (e.g., the algorithm conventionally utilized for ECG R-wave detection). Time intervals can then be computed between any two successive cardiac beats. The time intervals, derived from the ECG signals, can be used to control the acquisition duration of the ECG signal (e.g. 3 cardiac cycles). The ECG signal may also be processed to remove chest compression artifact.

At step 306, a cardiac mechanical signal is detected. In some implementations, the cardiac mechanical signal is acquired simultaneous to the ECG signal. The cardiac mechanical signal can be received from any appropriate source of cardiac mechanical signal. For example, the cardiac mechanical signal can be received in real-time from an accelerometer, laser interferometer, elastic band, or other sensor for measuring chest wall motion characteristic of an intrinsic myocardial wall movement of the patient.

In some implementations, the cardiac mechanical signal can include an accelerometer signal measured by an accelerometer configured to detect chest movements of the patient during a chest compression pause, such as during ventilation or rhythm check. The detection can include processing the accelerometer signal to derive the intrinsic myocardial wall movement.

The processing algorithm of the cardiac mechanical signal includes the calibration of the intrinsic myocardial wall movement so that the baseline level is zero if no myocardial movement is detected. The negative value of the intrinsic myocardial wall movement can be flipped over to positive along zero line. The processed positive intrinsic myocardial wall movement can be processed by a band pass filter with the low cutoff in 0.05 Hz and the high cutoff being at the middle point between the base frequency and the $2^{nd}$ harmonic. The base frequency equals to the heart rate/60. The filter can eliminate $2^{nd}$ and high order harmonics, as well as the DC component. The filter can be based on the bidirectional design with linear phase response. In some implementations, the processing algorithm of the intrinsic myocardial wall movement includes identification of onset and duration of each cardiac ejection phase and each cardiac relaxation phase.

At step 308, an association between the ECG signal and the intrinsic myocardial wall movement is determined. For example, a crosscorrelation function can be calculated between ECG and processed intrinsic myocardial wall movement and the peak correlation coefficient (CCp) in the crosscorrelation function can be obtained. A significant correlation between the ECG signal and the processed intrinsic myocardial wall movement can be interpreted as an indication of myocardial contraction capable of perfusion. In some implementations, the identification of such myocardial contraction is based on the CCp exceeding a threshold value. The bigger the CCp the more likely the heart has myocardial contraction capable of perfusion and organized rhythm, as well as return of spontaneous circulation. The smaller the CCp the more likely the heart has non-perfusion rhythm, such as PEA. In some implementations, a CCp value between approximately 0.1 and 0.5 and preferably above 0.128 can indicate a myocardial contraction capable of perfusion.

In some implementations, performing the correlation includes determining a shape of a correlation function between the ECG signal and the intrinsic myocardial wall movement. For example, a correlation function characterized by a triangular shape can indicate the presence of myocardial contraction capable of perfusion. A correlation function characterized by an irregular shape (similar to background noise signal) can indicate persistence of PEA.

If the outcome of the correlation algorithm indicates persistence of PEA, the process continues to step 310. At step 310, the system provides a feedback to the user to apply a chest compressions and/or ventilations. In some implementations, the indicator can include a visual display on the monitoring device based on the identification of PEA and an alarm that alerts a user of the device. In some implementations, both the metronome rate and the compression prompts can be used simultaneously to guide the user in applying CPR. In some implementations, the chest compressions are performed by a mechanical chest compression device, e.g. A suction based compression-decompression device or a belt driven chest compression device. In additional implementations, an intrathoracic pressure regulation device may be used during CPR to enhance negative intrathoracic pressure and promote blood flow to the heart.

The steps 302 to 310 of the example process 300 can be repeated multiple times until the identification of the cardiac perfusion. If the outcome of the correlation algorithm indicates occurrence of myocardial contraction capable of perfusion, the process continues to step 312. At step 312, the system provides a feedback to the user of the device.

In some implementations, the feedback includes an indication to terminate CPR. In some implementations, the feedback includes an indication to synchronize one or more phasic resuscitative techniques (e.g., CPR, ventilation, abdominal counter pulsations, phasic limb compression, and electrical stimulation, among others, to augment cardiac ejection and filling) with the derived intrinsic myocardial wall movement. The feedback can be displayed on the monitoring device (e.g., monitoring device 106 of FIG. 1) and it can also include audio signals (e.g., instructions provided by a metronome rate and compression prompts). The timing, frequency and/or duration can be varied depending on the particular phasic resuscitative technique. The monitoring device 106 as shown in FIG. 1 can use one or more sensory inputs, and a logic circuit utilizing and indicator or indicators of efficacy, to optimize the effect of synchronization on hemodynamics.

For example, the feedback can guide the rescuer to synchronize CPR with the derived intrinsic myocardial wall movement. Chest compression rates and durations can be adjusted based on the intrinsic myocardial wall movement to augment cardiac ejection and prevent interfering with cardiac filling. The CPR synchronization can include applying a compressive force to the chest during a portion or the entire duration of the cardiac ejection phase and ceasing compressions during a portion or the entire duration of the cardiac relaxation phase. By applying synchronized therapy, cardiac output and organ profusion can be increased, thereby improving the outcome of patients with impaired hemodynamics.

As another example, the feedback can guide the rescuer to synchronize ventilations with the intrinsic myocardial wall movement. For example, inspiration and expiration can be synchronized with the intrinsic myocardial wall movement to optimize the increase in cardiac output. For instance, inspiration can be synchronized to systole and expiration can be synchronized to with diastole. The synchronized ventilations can be applied by a traditional ventilator or manually, such as by using a ventilatory bag.

Figure 4:
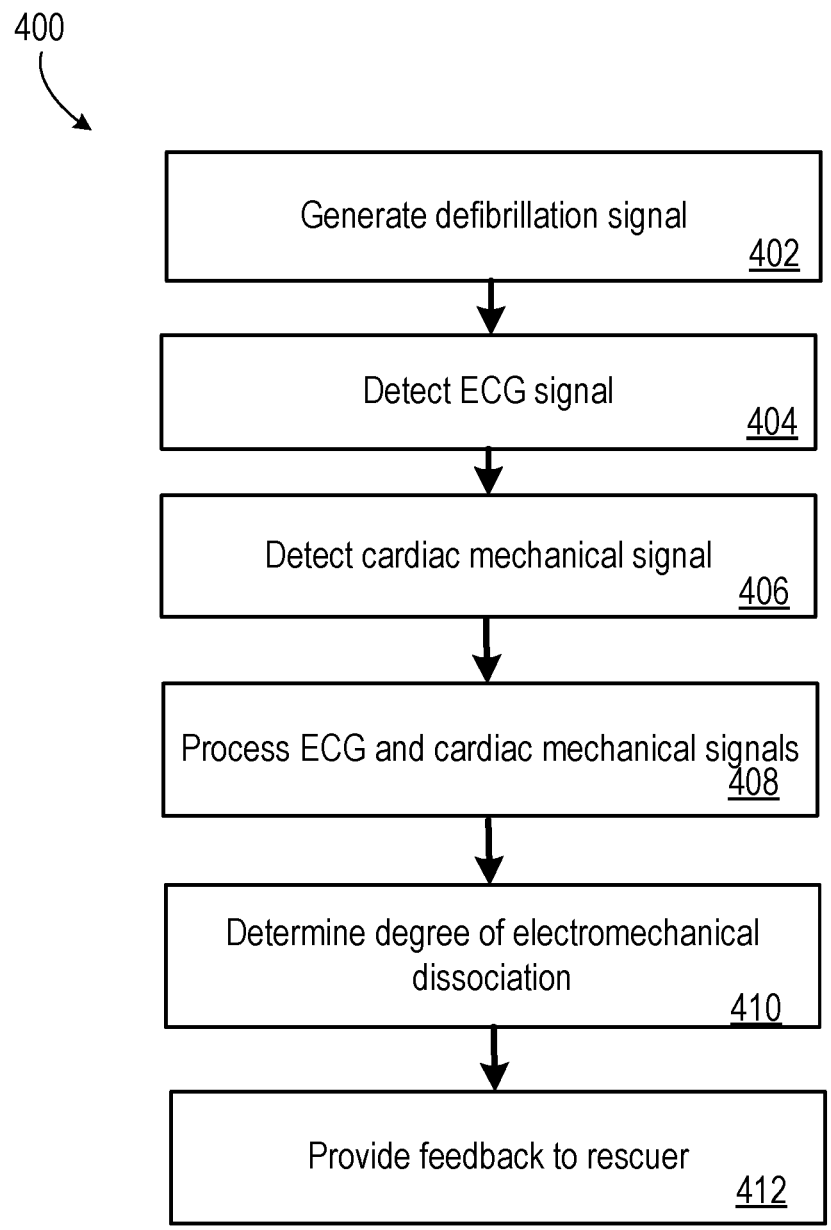
FIG. 4 is a flow chart of another example process for assisting with CPR treatment.

In some implementations, if the feedback provides guidance for synchronized phasic resuscitative techniques the steps 302 to 312 of the example process 300 can be repeated multiple times to determine the efficiency of the synchronization. For example, an increase of the correlation coefficient can be used as an indicator of efficient synchronization and a decrease of the correlation coefficient can be used as an indicator of inefficient synchronization. In case of efficient synchronization, the feedback parameters (e.g., timing, frequency and/or duration of the applied phasic resuscitative technique) can be maintained constant. In case of inefficient synchronization, the feedback parameters (e.g., timing, frequency and/or duration of the applied phasic resuscitative technique) can be varied or the user can be prompted to terminate previously synchronized phasic resuscitative technique FIG. 4 shows an example process 400 for assisting with CPR treatment based on identification of cardiac perfusion. In some implementations, the method 400 is implemented by the example patient monitoring device described herein with reference to FIGS. 1 and 2. However, other implementations are possible.

At step 402, a defibrillation signal is generated to treat cardiac arrest in a patient. For example, defibrillation pads are attached to the patient to provide electrotherapy during the CPR treatment. Electrotherapy can include delivery of a therapeutic defibrillation current of standard or particularly selected duration, frequency and voltage.

At step 404, an ECG signal is detected. The ECG signal can be received from any appropriate source of patient ECG data, as described with reference to FIGS. 1 and 3. At step 406, a cardiac mechanical signal (e.g., accelerometer signal) is detected. In some implementations, the cardiac mechanical signal is acquired simultaneous to the ECG signal. The cardiac mechanical signal can be received from any appropriate source of cardiac mechanical signal, as described with reference to FIGS. 1 and 3. For example, the cardiac mechanical signal can be detected using a motion sensor (e.g. Accelerometer) placed on the patient's chest during a time when chest compressions are not being delivered to the patient.

At step 408, the ECG signal and the cardiac mechanical signal are processed. For example, the ECG and cardiac mechanical signal can be processed to filter the ECG and to extract the intrinsic myocardial wall movement of the patient. In some implementations, the processing algorithm includes determining the time delay between the ECG signal and the intrinsic myocardial wall movement. In some implementations, the processing algorithm includes determining the magnitude of the intrinsic myocardial wall movement. The time delay and/or the magnitude of the intrinsic myocardial wall movement can be determined as an average or median over a selected number of cardiac cycles. A variation trend of the time delay and/or the magnitude of the intrinsic myocardial wall movement can also be determined for a selected number of cardiac cycles.

At step 410, a degree of electromechanical dissociation between the input from the sensor and the ECG signal is determined. The electromechanical dissociation can be expressed in percentages, 0% indicating cardiac perfusion and 100% indicating maximum PEA. The electromechanical dissociation can be divided in three groups: mild (e.g., <30%), moderate (e.g., 30-50%) and severe (>50%). In some implementations, the degree of electromechanical dissociation is determined based on the magnitude of the intrinsic myocardial wall movement and/or the time delay between the ECG signal and the intrinsic myocardial wall movement. In some implementations, the magnitude of the intrinsic myocardial wall movement can be compared to one or more pre-selected magnitude thresholds to quantify the electromechanical dissociation. For example, the magnitude threshold can be between about 0.015 G and 0.03 G to indicate cardiac movement indicative of perfusion. In some implementations, the time delay can be normalized to the duration of the cardiac cycle to quantify the electromechanical dissociation. For example, if the time delay between the ECG signal and the intrinsic myocardial wall movement is between about 125 and 250 milliseconds the electromechanical dissociation can be classified as mild, if the time delay is between about 250 millisecond and 500 millisecond the electromechanical dissociation can be classified as moderate, and if the time delay is above about 500 millisecond the electromechanical dissociation can be classified as severe.

The degree of electromechanical dissociation can be used to determine whether to synchronize CPR to the cardiac cycle or whether to continue CPR. Referring to FIG. 5, if a myocardial contraction capable of perfusion is determined based on a correlation between the ECG and intrinsic myocardial wall movement, manual or mechanical CPR, including chest compressions, may be stopped. Alternatively, a degree of electromechanical dissociation may be determined. Where the degree of mechanical dissociation is determined to be mild, CPR, such as chest compressions, may be synchronized to the cardiac cycle. Where the degree is determined to be mild, chest compressions may be modified to reduce the depth of compression (i.e. To provide softer compressions).

Referring now to FIG. 4, at step 412, the system provides a feedback to the user based on the determined electromechanical dissociation. The feedback can include at least one of an indication to stop chest compressions, an indication to synchronize chest compression to cardiac systole (as described with reference to FIG. 3), an indication to provide softer compressions, or an indication to continue chest compressions, an indication to synchronize ventilation to the cardiac cycle (e.g. by providing positive pressure ventilation during systole and exhalation during diastole), etc. In some implementations, a negative intrathoracic pressure regulation device may be used during CPR. The feedback can be audible, visual and/or tactile feedback, as described with reference to FIG. 1. For example, where the degree of electromechanical dissociation is mild, the user may be prompted to synchronize chest compressions to cardiac systole. The user may also, or in the alternative, be prompted to provide softer compressions. The user may further be prompted to synchronize ventilation to the cardiac cycle.

In some implementations, the synchronization of chest compressions with cardiac systole and/or diastole can be accomplished using a mechanical chest compression device. A controller of such a mechanical chest compression device may be configured to synchronize the intrinsic myocardial wall movement and chest compressions to provide compressions during systole. The device may also be configured to provide softer compressions when mild electromechanical dissociation is determined. A mechanical ventilator may also be configured to synchronize providing ventilation to the cardiac cycle.

Multiple sensors may be employed in synchronizing chest compressions and/or ventilations to the cardiac cycle. For example, the ECG signal may be processed to define the onset of systole, either by itself or in combination with the signal corresponding to the intrinsic myocardial wall movement. Additional sensors capable of detecting blood flow and/or ejection of blood from the heart may be used, for example, invasive or noninvasive blood pressure sensors, heart sound sensors, etc.

In some implementations, if the feedback provides guidance for synchronized phasic resuscitative techniques the steps 402 to 412 of the example process 400 can be repeated multiple times to determine the efficiency of the synchronization. For example, a decrease of the degree of electromechanical dissociation can be used as an indicator of efficient synchronization and an increase of the degree of electromechanical dissociation can be used as an indicator of inefficient synchronization. In case of efficient synchronization, the feedback parameters (e.g., timing, frequency and/or duration of the applied phasic resuscitative technique) can be maintained constant. In case of inefficient synchronization, the feedback can be modified. For example, to prevent augmentation of electromechanical dissociation, the synchronization parameters (e.g., timing, frequency and/or duration of the applied phasic resuscitative technique) can be varied or the user can be prompted to terminate previously synchronized phasic resuscitative technique.

Figure 5A:
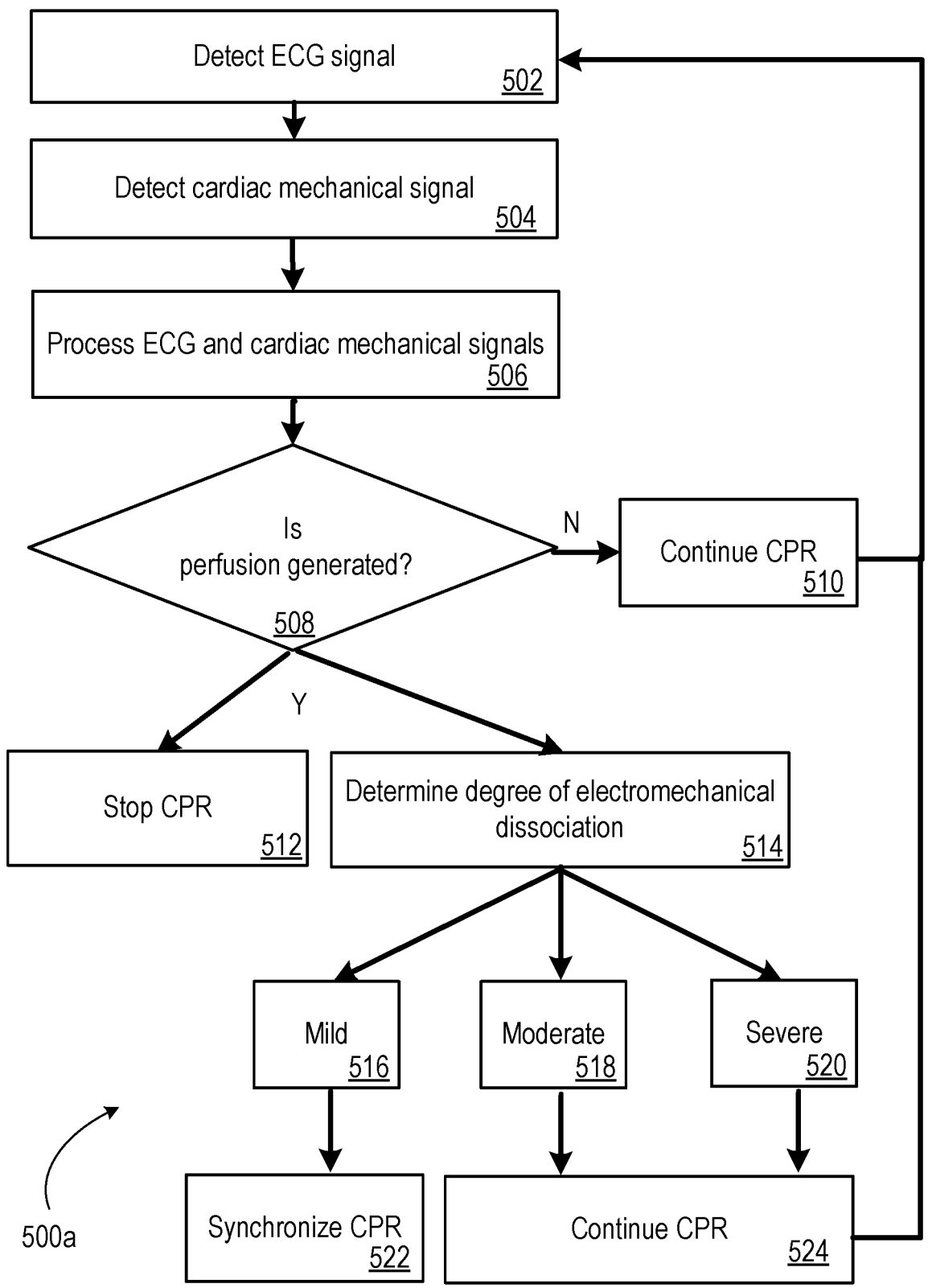
FIG. 5A is a flow chart of another example process for assisting with CPR treatment.

FIG. 5A shows an example process 500*a* for assisting with CPR treatment based on identification of cardiac perfusion. In some implementations, the method 500*a* is implemented by the example patient monitoring device described herein with reference to FIGS. 1 and 2. However, other implementations are possible.

At step 502, an ECG signal is detected. The ECG signal can be received from any appropriate source of patient ECG data, as described with reference to FIGS. 1 and 3. At step 504, a cardiac mechanical signal is detected using one or more sensors described herein. In some implementations, the cardiac mechanical signal is acquired simultaneous to the ECG signal. The cardiac mechanical signal can be received from any appropriate source of cardiac mechanical signal, as described with reference to FIGS. 1 and 4.

At step 506, the ECG signal and the cardiac mechanical signal are processed to extract the intrinsic myocardial wall movement, as described with reference to FIG. 4. At step 508, it is determined whether the intrinsic myocardial wall movement indicates movement capable of perfusion (e.g., if cardiac output exceeds a threshold associated to minimum perfusion). If it is determined that perfusion is not generated, the process continues CPR at step 510 and repeats steps 502 to 508. If it is determined that perfusion is generated, the process is finalized at step 512, by terminating CPR, or continues to step 514.

At step 514, a degree of electromechanical dissociation between the intrinsic myocardial wall movement and the ECG signal is determined. The electromechanical dissociation can be quantitatively or qualitatively expressed. At step 516, the electromechanical dissociation is compared to a first threshold to determine whether the electromechanical dissociation is mild (e.g., <250 milliseconds). At step 518, the electromechanical dissociation is compared to the first and a second threshold to determine whether the electromechanical dissociation is moderate (e.g., 250 millisecond and 500 millisecond). At step 518, the electromechanical dissociation is compared to the second threshold to determine whether the electromechanical dissociation is severe (>500 millisecond). If the determined electromechanical dissociation is mild, the process continues to step 522 to synchronize CPR, as described with reference to FIGS. 3 and 4. If the determined electromechanical dissociation is moderate or severe, the process continues to step 524 to continue CPR and the previous steps of the process 500*a* can be repeated.

Figure 5B:
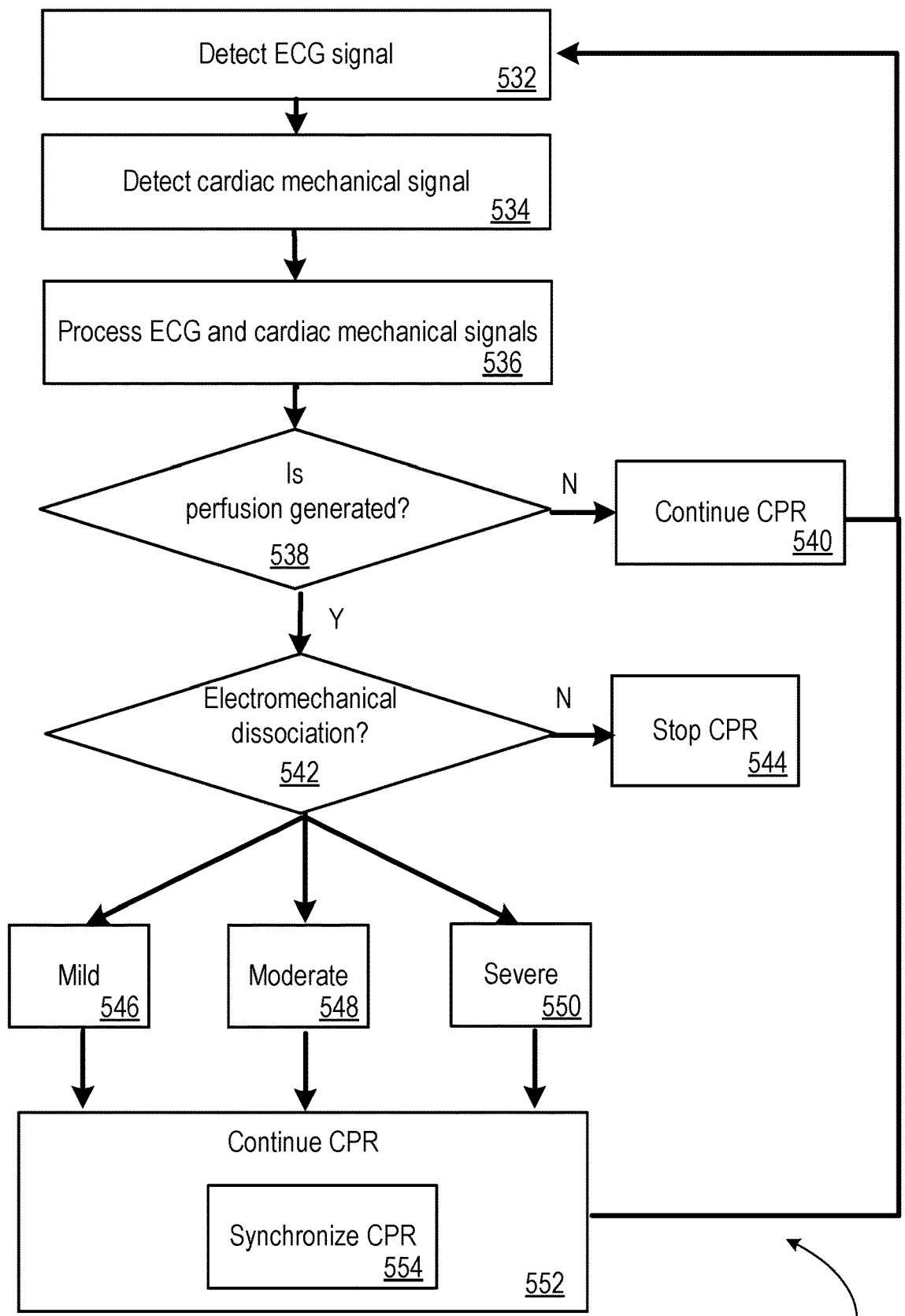
FIG. 5B is a flow chart of another example process for assisting with CPR treatment.

FIG. 5B shows an example process 500b for assisting with CPR treatment based on identification of cardiac perfusion. In some implementations, the method 500b is implemented by the example patient monitoring device described herein with reference to FIGS. 1 and 2. However, other implementations are possible.

At step 532, an ECG signal is detected. The ECG signal can be received from any appropriate source of patient ECG data, as described with reference to FIGS. 1 and 3. At step 534, a cardiac mechanical signal is detected using one or more sensors described herein. In some implementations, the cardiac mechanical signal is acquired simultaneously to the ECG signal. The cardiac mechanical signal can be received from any appropriate source of cardiac mechanical signal, as described with reference to FIGS. 1 and 4.

At step 536, the ECG signal and the cardiac mechanical signal are processed to extract the intrinsic myocardial wall movement, as described with reference to FIG. 4. At step 538, it is determined whether the intrinsic myocardial wall movement indicates a movement capable of perfusion (e.g., if cardiac output exceeds a threshold associated to minimum perfusion). If it is determined that perfusion is not generated, the process continues CPR at step 540 and repeats steps 532 to 538. If it is determined that perfusion is generated, the process is finalized at step 544, by terminating CPR, or continues to the classification of electromechanical dissociation as mild 546 (e.g., <250 milliseconds), moderate 548 (e.g., 250 millisecond and 500 millisecond) or severe 550 (>500 millisecond) and continue CPR at step 552. In some implementations, step 552 includes the option of synchronizing CPR with the ECG signal, which forms step 554. In some cases, a low rate limit for synchronized chest compressions may be employed. For example, if the rate of PEA is too slow (e.g., lower than 60), synchronized chest compressions may not be effective. Accordingly, when the rate of synchronized compressions for PEA is below the low rate limit, or if a time period beyond a threshold time has elapsed without having received an indication of a synchronized PEA beat, the system may issue a mandatory non-synchronized chest compression, so that chest compressions may be suitably applied.

Figure 5C:
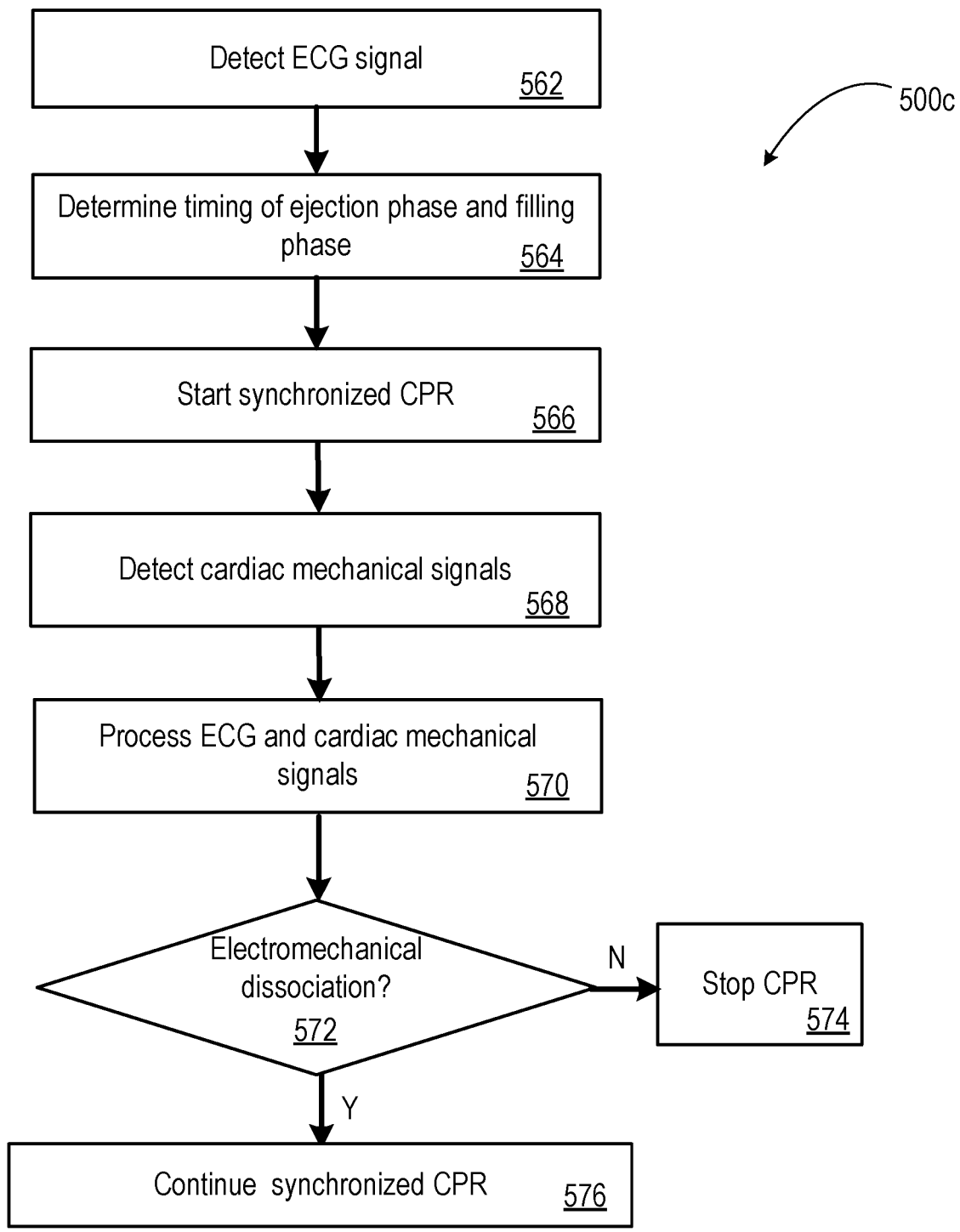
FIG. 5C is a flow chart of another example process for assisting with CPR treatment.

FIG. 5C shows an example process 500c for assisting with CPR treatment based on identification of cardiac perfusion. In some implementations, the method 500c is implemented by the example patient monitoring device described herein with reference to FIGS. 1 and 2. However, other implementations are possible. At step 562, an ECG signal is detected. The ECG signal can be received from any appropriate source of patient ECG data, as described with reference to FIGS. 1 and 3. At step 564, the ECG signal is used to determine the timing of the ejection phase and the filling phase.

At step 566, synchronized CPR can be started. Synchronized CPR can include chest compressions and ventilations with timing, frequency and/or duration that may be varied depending on the particular treatment. For example, chest compressions can be performed during the entire systolic phase, or during a portion of the systolic phase. Chest compressions can be performed during every systolic phase or during particularly selected systolic phases. Chest compressions can be synchronized with the ejection phase so that the compressive forces do not interfere with the refilling phase. The active delivery of ventilations can be synchronized with the sensed ejection phases and refilling phases. Ventilations can be coordinated with the application of the chest compressions. The signals provided by one or more sensors (e.g., sensors 102a and 102b described with reference to FIGS. 1A and 1B) can be used to optimize CPR synchronization.

At step 568, a cardiac mechanical signal is detected. In some implementations, the cardiac mechanical signal is acquired simultaneous to the ECG signal. The cardiac mechanical signal can be received from any appropriate source of cardiac mechanical signal, as described with reference to FIGS. 1 and 4.

At step 570, the ECG signal and the cardiac mechanical signal are processed, as described with reference to FIG. 4. For example, the ECG signal can be filtered and the cardiac mechanical signal can be processed to extract the intrinsic myocardial wall movement. The processing can further include analyzing the force, timing and vector of chest compression relative to the ECG signal, to evaluate the accuracy of CPR synchronization. At step 572, it is determined whether the intrinsic myocardial wall movement indicates movement capable of perfusion (e.g., if cardiac output exceeds a threshold associated to minimum perfusion). If it is determined that perfusion is generated, the process is finalized at step 574, by terminating CPR. If it is determined that perfusion is not generated, the process continues synchronized CPR at step 576. In some implementations, the ECG signal and the cardiac mechanical signal are processed for each cardiac cycle, such that CPR synchronization can be performed in real-time. A variable time delay can be added in response to a change identified in the ECG signal, such that CPR synchronization can be finely adjusted to ECG changes.

Each of the processes 500a, 500b, and 500c, described with reference to FIGS. 5A-5C can include a step to provide the patient with medications and additional phasic therapies, as part of the CPR treatment synchronized with residual myocardial activity. Examples of medications that can be applied include epinephrine, vasopressin, amiodarone, and the like. Examples of phasic therapies can include, among others: abdominal counterpulsation, ventilation, phasic limb-compression, myocardial electrical stimulation, intravascular fluid shifting, intravascular balloon inflation-deflation, application of transthoracic electromagnetic irradiation.

An experimental study, using the methods described with reference to FIGS. 5A-5C was performed in seven porcine models of post countershock pulseless electrical activity. A total of 32 matched synchronization pairs were obtained from the porcine models. The PEA pulse pressure was 2.47+2.34 mmHg and the PEA rate was 74+16.5. Chest compression synchronized with R wave maintained carotid blood flow (53.6 vs. 46.7, p=0.11), maintained coronary perfusion pressure (15.6 vs. 16.6 mmHg, p=0.34), and increased carotid blood flow stroke volume (=CBF/PEA rate) (0.76 vs. 0.47 ml, p=0.0004) as compared to standard chest compression. During near complete electromechanical dissociation (true PEA), synchronization of external chest compression with R waves maintained carotid blood flow and coronary perfusion pressure despite lower compression rates as compared to standard chest compression without synchronization.

Figure 6:
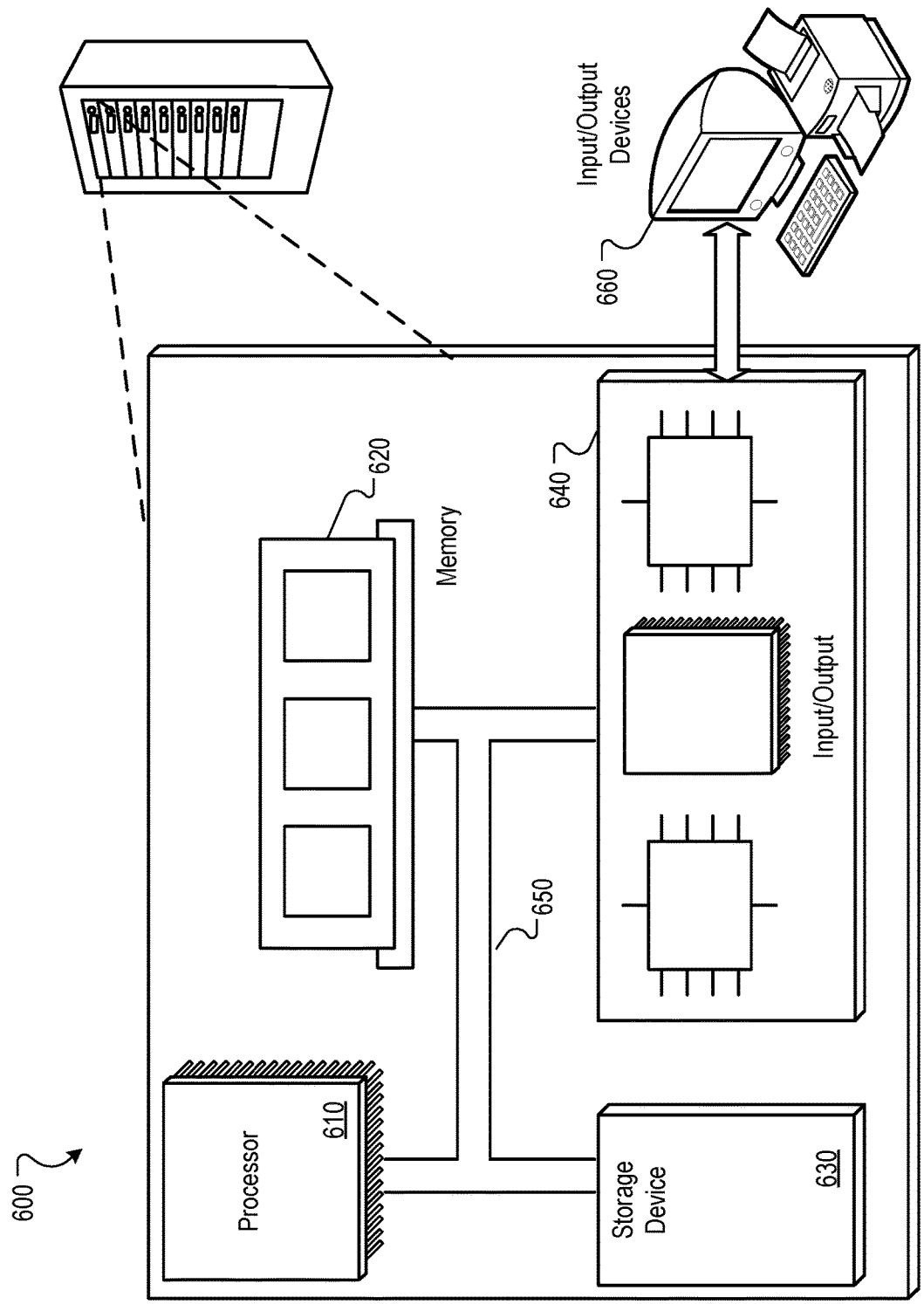
FIG. 6 is a schematic illustration of another example system for assisting with CPR treatment.

FIG. 6 is a block diagram of an example computer system 600. For example, referring to FIG. 2, computer systems 226 could be an example of the system 600 described here, as could the monitoring device 106 as shown in FIG. 1, as could a computer system used by any of the users who interact with the monitoring device 106 as shown in FIG. 1. The system 600 includes a processor 610, a memory 620, a storage device 630, and one or more input/output interface devices 640. Each of the components 610, 620, 630, and 640 can be interconnected, for example, using a system bus 650.

The processor 610 is capable of processing instructions for execution within the system 600. The term "execution" as used here refers to a technique in which program code causes a processor to carry out one or more processor instructions. In some implementations, the processor 610 is a single-threaded processor. In some implementations, the processor 610 is a multi-threaded processor. In some implementations, the processor 610 is a quantum computer. The processor 610 is capable of processing instructions stored in the memory 620 or on the storage device 630. The processor 610 can execute operations such as assistance of CPR treatment.

The memory 620 stores information within the system 600. In some implementations, the memory 620 is a computer-readable medium. In some implementations, the memory 620 is a volatile memory unit. In some implementations, the memory 620 is a non-volatile memory unit.

The storage device 630 is capable of providing mass storage for the system 600. In some implementations, the storage device 630 is a non-transitory computer-readable medium. In various different implementations, the storage device 630 can include, for example, a hard disk device, an optical disk device, a solid-date drive, a flash drive, magnetic tape, or some other large capacity storage device. In some implementations, the storage device 630 can be a cloud storage device, e.g., a logical storage device including one or more physical storage devices distributed on a network and accessed using a network, such as the network 206 shown in FIG. 2. In some examples, the storage device can store long-term data, such as data described in this application as stored on a patient information system 224 as shown in FIG. 2. The input/output interface devices 640 provide input/output operations for the system 600. In some implementations, the input/output interface devices 640 can include one or more of a network interface devices, e.g., an Ethernet interface, a serial communication device, e.g., an RS-232 interface, and/or a wireless interface device, e.g., an 802.11 interface, a 3G wireless modem, a 4G wireless modem, etc. A network interface device allows the system 600 to communicate, for example, transmit and receive data such as data described in this application as being communicated by way of a network 206 as shown in FIG. 2. In some implementations, the input/output device can include driver devices configured to receive input data and send output data to other input/output devices, e.g., keyboard, printer and display devices 660. In some implementations, mobile computing devices, mobile communication devices, and other devices can be used.

Referring to FIGS. 3-5, computer program modules can be realized by instructions that upon execution cause one or more processing devices to carry out the processes and functions described above, for example, assistance of CPR. Such instructions can include, for example, interpreted instructions such as script instructions, or executable code, or other instructions stored in a computer readable medium.

A server 232 as shown in FIG. 2 can be distributively implemented over a network, such as a server farm, or a set of widely distributed servers or can be implemented in a single virtual device that includes multiple distributed devices that operate in coordination with one another. For example, one of the devices can control the other devices, or the devices can operate under a set of coordinated rules or protocols, or the devices can be coordinated in another fashion. The coordinated operation of the multiple distributed devices presents the appearance of operating as a single device.

In some examples, the system 600 is contained within a single integrated circuit package. A system 600 of this kind, in which both a processor 610 and one or more other components are contained within a single integrated circuit package and/or fabricated as a single integrated circuit, is sometimes called a microcontroller. In some implementations, the integrated circuit package includes pins that correspond to input/output ports, e.g., that can be used to communicate signals to and from one or more of the input/output interface devices 640.

Although an example processing system has been described in FIG. 2, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as storing, maintaining, and displaying artifacts can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, or a combination of one or more of them.

The term "system" can encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM, DVD-ROM, and Blu-Ray disks. The processor and the memory can be supplemented by, or incorporated in, special purpose logic circuitry. Sometimes a server (e.g., server 232 as shown in FIG. 2) is a general purpose computer, and sometimes it is a custom-tailored special purpose electronic device, and sometimes it is a combination of these things. Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network such as the network 206 shown in FIG. 2. Examples of communication networks include a local area network ("LAN") and a wide area network ("WAN"), e.g., the Internet.

The systems and processes described with reference to FIGS. 1-6 can be used for performing statistical studies of cardiac mechanics. For example, a study can be performed using an out-hospital cardiac arrest database. A first set of data including a particular number of samples (e.g., 20) can be arbitrarily selected from pre-shock pause with VF as the underlying rhythm. The first set of data can represent the non-perfusion rhythm. A second set of data including a proportionally similar number of samples (e.g., 25) can be arbitrarily selected from post-shock pause for rhythm check with organized rhythms. The organized rhythms can be confirmed as corresponding to perfusion rhythms (e.g., based on the database annotations that the systolic blood pressure measurement was greater than 100 mmHg).

In some implementations, the performance of the described technique can be evaluated by classical ROC analysis. For example, a cutoff value of 0.128 in CCp can yield a balanced performance of 0.7 in sensitivity, specificity and PPV. The test can demonstrate that the accelerometer for CPR quality monitoring (CPR feedback) can be used to detect myocardial contraction during compression pause by using adaptive low pass filtering and cross correlation function calculation.

Many other implementations other than those described may be employed, and may be encompassed by the following claims.

What is claimed is:

1. A system for assisting with a cardiopulmonary resuscitation (CPR) treatment to be administered to a patient, the system comprising:
   electrodes configured to obtain an ECG signal from the patient;
   at least one motion sensor configured to measure an intrinsic myocardial wall movement of the patient; and
   one or more processors configured for
      during administration, to the patient, of chest compressions of the CPR treatment, receiving an input signal from the at least one motion sensor, as the motion sensor is moving with a chest wall to which it is coupled;
      comparing the input signal from the at least one motion sensor and the obtained ECG signal to determine a correlation between the input signal from the at least one motion sensor and the obtained ECG signal, to determine whether the intrinsic myocardial wall movement is indicative of a perfusion movement of patient's heart during chest compressions of the CPR treatment; and
      in response to determining that the intrinsic myocardial wall movement is indicative of the perfusion movement of the patient's heart during chest compressions of the CPR treatment, providing, by a user interface of the system, an indication to pause the chest compressions of the CPR treatment based on the determined intrinsic myocardial wall movement.

2. The system of claim 1, wherein the motion sensor comprises a velocity sensor.

3. The system of claim 1, wherein the motion sensor comprises an accelerometer.

4. The system of claim 1, wherein the at least one motion sensor comprises at least one of a laser interferometer and an elastic band configured to measure chest wall motion.

5. The system of claim 1, wherein the correlation between the ECG signal and the intrinsic myocardial wall movement comprises a temporal relationship between the input signal from the at least one motion sensor and the ECG signal.

6. The system of claim 1, wherein performing the correlation comprises determining a peak correlation coefficient between the ECG signal and the intrinsic myocardial wall movement.

7. The system of claim 6, wherein processing comprises comparing the peak correlation coefficient to a threshold that is between approximately 0.1 and 0.5.

8. The system of claim 7, wherein determining whether the intrinsic myocardial wall movement is indicative of the perfusion movement corresponds to the peak correlation coefficient exceeding the threshold.

9. The system of claim 1, wherein performing the correlation comprises determining a shape of a correlation function between the ECG signal and the intrinsic myocardial wall movement.

10. The system of claim 9, wherein determining whether the intrinsic myocardial wall movement is indicative of the perfusion movement is indicated by the shape being triangular.

11. The system of claim 1, wherein the indication is indicating to stop chest compressions.

12. The system of claim 1, wherein the indication is indicating the perfusion movement during the chest compressions of the CPR treatment.

13. The system of claim 1, wherein the perfusion movement comprises one or both of a residual left heart movement or residual right heart movement.

14. The system of claim 1, comprising at least one of a mechanical compression device, an inflatable vest, a nerve stimulator, and a suction based compression-decompression device to administer the chest compressions of the CPR treatment.

15. The system of claim 1, comprising a defibrillator configured to provide electrotherapy.

16. The system of claim 1, wherein processing further comprises determining a degree of electromechanical dissociation between the input signal from the at least one motion sensor and the ECG signal.

17. The system of claim 16, wherein the degree of electromechanical dissociation is determined based on a magnitude of the intrinsic myocardial wall movement.

18. The system of claim 16, wherein the degree of electromechanical dissociation is determined based on a time delay between the ECG signal and the intrinsic myocardial wall movement.

19. The system of claim 16, wherein the degree of electromechanical dissociation is determined based on a magnitude of the intrinsic myocardial wall movement and a time delay between the ECG signal and the intrinsic myocardial wall movement.

20. The system of claim 1, wherein the indication comprises a first indication to stop chest compressions at a first time and a second indication to continue chest compressions at a second time.

21. The system of claim 1, wherein the intrinsic myocardial wall movement of the patient is detected during a period when CPR chest compressions are not being delivered.

22. The system of claim 1, wherein the indication comprises at least one of stopping chest compressions and synchronizing chest compressions to cardiac systole.

23. The system of claim 22, further comprising a respiratory device configured to provide ventilations, wherein the indication further comprises synchronizing the ventilations to cardiac cycles.

24. The system of claim 22, wherein the chest compressions comprise manual chest compressions and the indication is indicated to a rescuer by a prompt.

25. The system of claim 22, wherein the chest compressions are delivered by a mechanical chest compression device and wherein a controller of the mechanical chest compression device is configured to stop chest compressions or synchronize chest compression to cardiac systole upon receiving the indication.

26. The system of claim 22, further comprising an intrathoracic pressure regulation device configured to enhance negative intrathoracic pressure to promote blood flow into the patient's heart.

* * * * *